(12) United States Patent
Deschenes et al.

(10) Patent No.: US 7,799,787 B2
(45) Date of Patent: Sep. 21, 2010

(54) HETEROAROMATIC COMPOUNDS AS INHIBITORS OF STEAROYL-COENZYME A DELTA-9 DESATURASE

(75) Inventors: Denis Deschenes, Dorval (CA); Rejean Fortin, Montreal (CA); Chun Sing Li, Dollard-des-Ormeaux (CA); Renata M. Oballa, Kirkland (CA); Yeeman K. Ramtohul, Pierrefonds (CA)

(73) Assignee: Merck Frosst Canada Ltd., Quebec (CA)

( * ) Notice: Subject to any disclaimer, the term of this patent is extended or adjusted under 35 U.S.C. 154(b) by 84 days.

(21) Appl. No.: 12/086,023

(22) PCT Filed: Dec. 18, 2006

(86) PCT No.: PCT/CA2006/002053
§ 371 (c)(1),
(2), (4) Date: Jun. 4, 2008

(87) PCT Pub. No.: WO2007/071023
PCT Pub. Date: Jun. 28, 2007

(65) Prior Publication Data
US 2009/0088431 A1    Apr. 2, 2009

(51) Int. Cl.
| | | |
|---|---|---|
| C07D 401/04 | (2006.01) | |
| A61K 31/501 | (2006.01) | |
| A61P 9/00 | (2006.01) | |
| A61P 9/10 | (2006.01) | |
| A61P 35/00 | (2006.01) | |
| A61P 3/10 | (2006.01) | |
| A61P 3/04 | (2006.01) | |
| A61P 3/00 | (2006.01) | |
| A61P 1/16 | (2006.01) | |

(52) U.S. Cl. .................. 514/252.03; 514/252.05; 544/238

(58) Field of Classification Search .......... 544/238; 514/252.03
See application file for complete search history.

(56) References Cited

U.S. PATENT DOCUMENTS

2009/0088431 A1*  4/2009  Deschenes et al. ....... 514/236.5
2009/0176793 A1*  7/2009  Hohlweg ............... 514/252.02
2009/0186876 A1*  7/2009  Brickmann et al. ......... 514/218

FOREIGN PATENT DOCUMENTS

| CA | 2 533 900 A1 | 2/2005 |
|---|---|---|
| CA | 2 533 901 A1 | 2/2005 |
| CA | 2 542 807 A1 | 4/2005 |
| WO | WO 2004/009091 A1 | 1/2004 |
| WO | WO 2006/034279 A1 | 3/2006 |
| WO | WO 2006/034312 A1 | 3/2006 |
| WO | WO 2006/034338 A1 | 3/2006 |
| WO | WO 2006/034341 A2 | 3/2006 |
| WO | WO 2006/034341 A3 | 3/2006 |
| WO | WO 2006/034440 A2 | 3/2006 |
| WO | WO 2006/034440 A3 | 3/2006 |
| WO | WO 2006/086445 A2 | 8/2006 |
| WO | WO 2006/086445 A3 | 8/2006 |
| WO | WO 2006/130986 A1 | 12/2006 |
| WO | WO 2007/009236 A1 | 1/2007 |
| WO | WO 2007/056846 A1 | 5/2007 |
| WO | WO 2008/017161 A1 | 2/2008 |

OTHER PUBLICATIONS

Dobrzyn, et al., Obesity Rev. 6, 169-174, 2005.*
Giutiérrez-Juárez, et al., J. Clin. Invest., vol. 116, No. 6, Jun. 2006, pp. 1686-1695.*

* cited by examiner

*Primary Examiner*—James O Wilson
*Assistant Examiner*—Cecilia M Jaisle
(74) *Attorney, Agent, or Firm*—Philippe L. Durette; John C. Todaro

(57) ABSTRACT

Heteroaromatic compounds of structural formula (I) are selective inhibitors of stearoyl-coenzyme A delta-9 desaturase (SCD1) relative to other known stearoyl-coenzyme A desaturases. The compounds of the present invention are useful for the prevention and treatment of conditions related to abnormal lipid synthesis and metabolism, including cardiovascular disease, such as atherosclerosis; lipid disorders; obesity; diabetes; neurological disease; metabolic syndrome; insulin resistance; fatty liver disease and cancer.

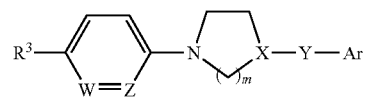

(I)

6 Claims, No Drawings

HETEROAROMATIC COMPOUNDS AS INHIBITORS OF STEAROYL-COENZYME A DELTA-9 DESATURASE

FIELD OF THE INVENTION

The present invention relates to heteroaromatic compounds which are inhibitors of stearoyl-coenzyme A delta-9 desaturase (SCD) and the use of such compounds to control, prevent and/or treat conditions or diseases mediated by SCD activity. The compounds of the present invention are useful for the control, prevention and treatment of conditions and diseases related to abnormal lipid synthesis and metabolism, including cardiovascular disease, such as atherosclerosis; dyslipidemia; obesity; diabetes; neurological disease; metabolic syndrome; insulin resistance; cancer; and hepatic steatosis.

BACKGROUND OF THE INVENTION

At least three classes of fatty acyl-coenzyme A (CoA) desaturases (delta-5, delta-6 and delta-9 desaturases) are responsible for the formation of double bonds in mono- and polyunsaturated fatty acyl-CoAs derived from either dietary sources or de novo synthesis in mammals. The delta-9 specific stearoyl-CoA desaturases (SCDs) catalyze the rate-limiting formation of the cis-double bond at the C9-C10 position in monounsaturated fatty acyl-CoAs. The preferred substrates are stearoyl-CoA and palmitoyl-CoA, with the resulting oleoyl and palmitoleoyl-CoA as the main components in the biosynthesis of phospholipids, triglycerides, cholesterol esters and wax esters (Dobrzyn and Natami, *Obesity Reviews*, 6: 169-174 (2005)).

The rat liver microsomal SCD protein was first isolated and characterized in 1974 (Strittmatter et al., *PNAS*, 71: 4565-4569 (1974)). A number of mammalian SCD genes have since been cloned and studied from various species. For example, two genes have been identified from rat (SCD1 and SCD2, Thiede et al., *J. Biol. Chem.*, 261, 13230-13235 (1986)), Mihara, K., *J. Biochem.* (Tokyo), 108: 1022-1029 (1990)); four genes from mouse (SCD1, SCD2, SCD3 and SCD4) (Miyazaki et al., *J. Biol. Chem.*, 278: 33904-33911 (2003)); and two genes from human (SCD1 and ACOD4 (SCD2)), (Zhang, et al., *Biochem. J.*, 340: 255-264 (1991); Beiraghi, et al., *Gene*, 309: 11-21 (2003); Zhang et al., *Biochem. J.*, 388: 135-142 (2005)). The involvement of SCDs in fatty acid metabolism has been known in rats and mice since the 1970's (Oshino, N., *Arch. Biochem. Biophys.*, 149: 378-387 (1972)). This has been further supported by the biological studies of a) Asebia mice that carry the natural mutation in the SCD1 gene (Zheng et al., *Nature Genetics*, 23: 268-270 (1999)), b) SCD1-null mice from targeted gene deletion (Ntambi, et al., *PNAS*, 99: 11482-11486 (2002), and c) the suppression of SCD1 expression during leptin-induced weight loss (Cohen et al., *Science*, 297: 240-243 (2002)). The potential benefits of pharmacological inhibition of SCD activity has been demonstrated with anti-sense oligonucleotide inhibitors (ASO) in mice (Jiang, et al., *J. Clin. Invest.*, 115: 1030-1038 (2005)). ASO inhibition of SCD activity reduced fatty acid synthesis and increased fatty acid oxidation in primary mouse hepatocytes. Treatment of mice with SCD-ASOs resulted in the prevention of diet-induced obesity, reduced body adiposity, hepatomegaly, steatosis, postprandial plasma insulin and glucose levels, reduced de novo fatty acid synthesis, decreased the expression of lipogenic genes, and increased the expression of genes promoting energy expenditure in liver and adipose tissues. Thus, SCD inhibition represents a novel therapeutic strategy in the treatment of obesity and related metabolic disorders.

There is compelling evidence to support that elevated SCD activity in humans is directly implicated in several common disease processes. For example, there is an elevated hepatic lipogenesis to triglyceride secretion in non-alcoholic fatty liver disease patients (Diraison, et al., *Diabetes Metabolism*, 29: 478-485 (2003)); Donnelly, et al., *J. Clin. Invest.*, 115: 1343-1351 (2005)). The postprandial de novo lipogenesis is significantly elevated in obese subjects (Marques-Lopes, et al., *American Journal of Clinical Nutrition*, 73: 252-261 (2001)). There is a significant correlation between a high SCD activity and an increased cardiovascular risk profile including elevated plasma triglycerides, a high body mass index and reduced plasma HDL (Attie, et al., *J. Lipid Res.*, 43: 1899-1907 (2002)). SCD activity plays a key role in controlling the proliferation and survival of human transformed cells (Scaglia and Igal, *J. Biol. Chem.*, (2005)).

Other than the above mentioned anti-sense oligonucleotides, inhibitors of SCD activity include non-selective thiafatty acid substrate analogs [B. Behrouzian and P. H. Buist, *Prostaglandins, Leukotrienes, and Essential Fatty Acids*, 68: 107-112 (2003)], cyclopropenoid fatty acids (Raju and Reiser, *J. Biol. Chem.*, 242: 379-384 (1967)), certain conjugated long-chain fatty acid isomers (Park, et al., *Biochim. Biophys. Acta*, 1486: 285-292 (2000)) and a series of pyridazine derivatives disclosed in published international patent applications WO 2005/011653; WO 2005/011654; WO 2005/011656; WO 2005/011656; WO 2005/011657; and US Patent Application Publication 2005/0119251, all assigned to Xenon Pharmaceuticals, Inc.

The present invention is concerned with novel heteroaromatic compounds as inhibitors of stearoyl-CoA delta-9 desaturase which are useful in the treatment and/or prevention of various conditions and diseases mediated by SCD activity including those related, but not limited, to elevated lipid levels, as exemplified in non-alcoholic fatty liver disease, cardiovascular disease, obesity, diabetes, metabolic syndrome, and insulin resistance.

The role of stearoyl-coenzyme A desaturase in lipid metabolism has been described by M. Miyazaki and J. M. Ntambi, *Prostaglandins, Leukotrienes, and Essential Fatty Acids*, 68: 113-121 (2003). The therapeutic potential of the pharmacological manipulation of SCD activity has been described by A. Dobryzn and J. M. Ntambi, in "Stearoyl-CoA desaturase as a new drug target for obesity treatment," *Obesity Reviews*, 6: 169-174 (2005).

SUMMARY OF THE INVENTION

The present invention also relates to heteroaromatic compounds of structural formula I:

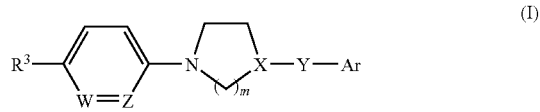

(I)

These heteroaromatic compounds are effective as inhibitors of SCD. They are therefore useful for the treatment, control or prevention of disorders responsive to the inhibition of SCD, such as diabetes, insulin resistance, lipid disorders, obesity, atherosclerosis, metabolic syndrome, and fatty liver disease.

The present invention also relates to pharmaceutical compositions comprising the compounds of the present invention and a pharmaceutically acceptable carrier.

The present invention also relates to methods for the treatment, control, or prevention of disorders, diseases, or conditions responsive to inhibition of SCD in a mammal in need thereof by administering the compounds and pharmaceutical compositions of the present invention.

The present invention also relates to methods for the treatment, control, or prevention of Type 2 diabetes, insulin resistance, obesity, lipid disorders, atherosclerosis, metabolic syndrome, and fatty liver disease in a mammal in need thereof by administering the compounds and pharmaceutical compositions of the present invention.

The present invention also relates to methods for the treatment, control, or prevention of obesity in a mammal in need thereof by administering the compounds of the present invention in combination with a therapeutically effective amount of another agent known to be useful to treat the condition.

The present invention also relates to methods for the treatment, control, or prevention of Type 2 diabetes in a mammal in need thereof by administering the compounds of the present invention in combination with a therapeutically effective amount of another agent known to be useful to treat the condition.

The present invention also relates to methods for the treatment, control, or prevention of atherosclerosis in a mammal in need thereof by administering the compounds of the present invention in combination with a therapeutically effective amount of another agent known to be useful to treat the condition.

The present invention also relates to methods for the treatment, control, or prevention of lipid disorders in a mammal in need thereof by administering the compounds of the present invention in combination with a therapeutically effective amount of another agent known to be useful to treat the condition.

The present invention also relates to methods for treating metabolic syndrome in a mammal in need thereof by administering the compounds of the present invention in combination with a therapeutically effective amount of another agent known to be useful to treat the condition.

DETAILED DESCRIPTION OF THE INVENTION

The present invention provides a method of inhibiting the delta-9 specific stearoyl-CoA desaturase (SCD) in a mammal in need thereof comprising administering to the mammal a therapeutically effective amount of a compound of structural formula I:

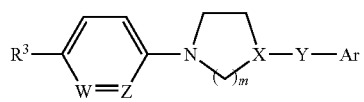

(I)

or a pharmaceutically acceptable salt thereof; wherein each n is independently 0, 1, 2, or 3;

each p is independently 0, 1, or 2;

m is 1, 2, or 3;

q is 1 or 2;

W and Z are N or CH, with the proviso that at least one of W and Z is N;

X—Y is CH—O, CH—S(O)$_p$, CH—NR$^6$, CH—C(R$^1$R$^2$)$_q$, or CH—C(O);

Ar is phenyl, naphthyl, or heteroaryl unsubstituted or substituted with one to five R$^8$ substituents;

R$^1$ and R$^2$ are each independently hydrogen or C$_{1-3}$ alkyl, wherein alkyl is unsubstituted or substituted with one to three substituents independently selected from fluorine and hydroxy;

R$^3$ is independently selected from the group consisting of
 C$_{1-6}$ alkyl, unsubstituted or substituted with one to five fluorines,
 C$_{3-7}$ cycloalkyl,
 C$_{1-6}$ alkoxy, unsubstituted or substituted with one to five fluorines,
 halogen,
 hydroxy,
 NR$^4$R$^5$,
 C≡N,
 CO$_2$R$^4$,
 C(O)NR$^4$R$^5$,
 OC(O)NR$^4$R$^5$,
 SO$_2$NR$^4$R$^5$,
 S(O)$_p$R$^6$,
 NR$^7$SO$_2$R$^6$,
 NR$^7$C(O)NR$^4$R$^5$,
 NR$^7$C(O)R$^6$, and
 NR$^7$CO$_2$R$^6$;

in which cycloalkyl is unsubstituted or substituted with one to three substituents independently selected from halogen, hydroxy, C$_{1-4}$ alkyl, trifluoromethyl, and C$_{1-4}$ alkoxy;

R$^4$ and R$^5$ are each independently selected from the group consisting of
 hydrogen,
 C$_{1-8}$ alkyl,
 (CH$_2$)$_n$-phenyl,
 (CH$_2$)$_n$-heteroaryl,
 (CH$_2$)$_n$-heterocyclyl
 (CH$_2$)$_n$-naphthyl, and
 (CH$_2$)$_n$C$_{3-7}$ cycloalkyl;

wherein alkyl, phenyl, heteroaryl, cycloalkyl, and heterocyclyl are unsubstituted or substituted with one to three groups independently selected from halogen, hydroxy, C$_{1-4}$ alkyl, C$_{1-4}$ alkoxy, —CO$_2$H, and —CONH$_2$; or R$^4$ and R$^5$ together with the nitrogen atom to which they are attached form a 4- to 8-membered mono- or bicyclic ring system optionally containing an additional heteroatom selected from O, S, NH, and NC$_{1-4}$ alkyl;

each R$^6$ is independently C$_{1-6}$ alkyl, wherein alkyl is unsubstituted or substituted with one to five substituents independently selected from halogen and hydroxyl;

R$^7$ is hydrogen or R$^6$; and each R$^8$ is independently selected from the group consisting of
 C$_{1-6}$ alkyl,
 (CH$_2$)$_n$-phenyl,
 (CH$_2$)$_n$-naphthyl,
 (CH$_2$)$_n$-heteroaryl,
 (CH$_2$)$_n$-heterocyclyl,
 (CH$_2$)$_n$C$_{3-7}$ cycloalkyl,
 halogen, $OR^4$,
$(CH_2)_n NR^4R^5$,
$(CH_2)_n C\equiv N$,
$(CH_2)_n CO_2R^4$,
$NO_2$,
$(CH_2)_n NR^7SO_2R^6$,
$(CH_2)_n SO_2NR^4R^5$,
$(CH_2)_n S(O)_p R^6$,
$(CH_2)_n NR^7C(O)NR^4R^5$,
$(CH_2)_n C(O)NR^4R^5$,
$(CH_2)_n NR^7C(O)R^6$,
$(CH_2)_n NR^7CO_2R^6$,
$O(CH_2)_n C(O)NR^4R^5$,
$CF_3$,
$CH_2CF_3$,
$OCF_3$, and
$OCH_2CF_3$;

in which phenyl, naphthyl, heteroaryl, cycloalkyl, and heterocyclyl are unsubstituted or substituted with one to three substituents independently selected from halogen, hydroxy, $C_{1-4}$ alkyl, trifluoromethyl, and $C_{1-4}$ alkoxy; and wherein any methylene ($CH_2$) carbon atom in $R^8$ is unsubstituted or substituted with one to two groups independently selected from halogen, hydroxy, and $C_{1-4}$ alkyl; or two substituents when on the same methylene ($CH_2$) group are taken together with the carbon atom to which they are attached to form a cyclopropyl group.

Inhibition of SCD is useful for the treatment, control or prevention of disorders responsive to the inhibition of SCD, such as diabetes, insulin resistance, lipid disorders, obesity, atherosclerosis, metabolic syndrome, and fatty liver disease.

In one embodiment of the methods of the present invention, m is 2.

In a second embodiment of the methods of the present invention, m is 1.

In a third embodiment of the methods of the present invention, W and Z are both N.

In a fourth embodiment of the methods of the present invention, W is N and Z is CH.

In a fifth embodiment of the methods of the present invention, W is CH and Z is N.

In a sixth embodiment of the methods of the present invention, X—Y is CH—O. In a class of this embodiment, Ar is phenyl unsubstituted or substituted with one to three $R^8$ substituents as defined above.

In a seventh embodiment of the methods of the present invention, X—Y is CH—S(O)$_p$. In a class of this embodiment, Ar is phenyl unsubstituted or substituted with one to three $R^8$ substituents as defined above.

In an eighth embodiment of the methods of the present invention, X—Y is CH—$NR^6$. In a class of this embodiment, Ar is phenyl unsubstituted or substituted with one to three $R^8$ substituents as defined above.

In a ninth embodiment of the methods of the present invention, X—Y is CH—C(O). In a class of this embodiment, Ar is phenyl unsubstituted or substituted with one to three $R^8$ substituents as defined above In a tenth embodiment of the methods of the present invention, X—Y is CH—$(CR^1R^2)_q$. In a class of this embodiment, q is 1 and Ar is phenyl unsubstituted or substituted with one to three $R^8$ substituents as defined above. In a class of this embodiment, q is 2 and Ar is phenyl unsubstituted or substituted with one to three $R^8$ substituents as defined above. In a third class of this embodiment, $R^1$ and $R^2$ are hydrogen and Ar is phenyl unsubstituted or substituted with one to three $R^8$ substituents.

In yet another embodiment of the methods of the present invention, m is 2; W and Z are N; X—Y is CH—O; and Ar is phenyl unsubstituted or substituted with one to three substituents independently selected from $R^8$ as defined above.

In yet another embodiment, $R^3$ is selected from the group consisting of
$C(O)NR^4R^5$,
$OC(O)NR^4R^5$,
$SO_2NR^4R^5$,
$NR^7SO_2R^6$,
$NR^7C(O)NR^4R^5$,
$NR^7C(O)R^6$, and
$NR^7CO_2R^6$;

wherein $R^4$, $R^5$, $R^6$, and $R^7$ are as defined above.

The present invention also provides novel heteroaromatic compounds useful as inhibitors of SCD. The novel compounds of the present invention are described by structural formula I:

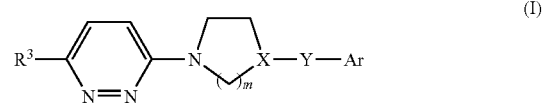

and pharmaceutically acceptable salts thereof; wherein each n is independently 0, 1, 2, or 3;

each p is independently 0, 1, or 2;

m is 1, 2, or 3;

q is 1 or 2;

X—Y is CH—O, CH—S(O)$_p$, CH—$NR^6$, CH—$C(R^1R^2)_q$, or CH—C(O);

Ar is phenyl, naphthyl, or heteroaryl unsubstituted or substituted with one to five $R^8$ substituents;

$R^1$ and $R^2$ are each independently hydrogen or $C_{1-3}$ alkyl, wherein alkyl is unsubstituted or substituted with one to three substituents independently selected from fluorine and hydroxy;

$R^3$ is independently selected from the group consisting of
$C(O)NR^4R^5$,
$OC(O)NR^4R^5$,
$SO_2NR^4R^5$,
$NR^7SO_2R^6$,
$NR^7C(O)NR^4R^5$,
$NR^7C(O)R^6$, and
$NR^7CO_2R^6$;

in which cycloalkyl is unsubstituted or substituted with one to three substituents independently selected from halogen, hydroxy, $C_{1-4}$ alkyl, trifluoromethyl, and $C_{1-4}$ alkoxy;

$R^4$ and $R^5$ are each independently selected from the group consisting of
hydrogen,
$C_{1-8}$ alkyl,
$(CH_2)_n$-phenyl,
$(CH_2)_n$-heteroaryl,
$(CH_2)_n$-naphthyl, and
$(CH_2)_n C_{3-7}$ cycloalkyl;

wherein alkyl, phenyl, heteroaryl, and cycloalkyl are unsubstituted or substituted with one to three groups independently selected from halogen, hydroxy, $C_{1-4}$ alkyl, and $C_{1-4}$ alkoxy; or $R^4$ and $R^5$ together with the nitrogen atom to which they are attached form a 4- to 8-membered mono- or bicyclic ring system optionally containing an additional heteroatom selected from O, S, NH, and $NC_{1-4}$ alkyl;

each $R^6$ is independently $C_{1-6}$ alkyl, wherein alkyl is unsubstituted or substituted with one to five substituents independently selected from halogen and hydroxyl;

$R^7$ is hydrogen or $R^6$; and each $R^8$ is independently selected from the group consisting of
$C_{1-6}$ alkyl,
$(CH_2)_n$-phenyl,
$(CH_2)_n$-naphthyl,
$(CH_2)_n$-heteroaryl,
$(CH_2)_n$-heterocyclyl,
$(CH_2)_n C_{3-7}$ cycloalkyl,
halogen,
$OR^4$,
$(CH_2)_n NR^4R^5$,
$(CH_2)_n C\equiv N$,
$(CH_2)_n CO_2R^4$,
$NO_2$,
$(CH_2)_n NR^7SO_2R^6$,
$(CH_2)_n SO_2NR^4R^5$,
$(CH_2)_n S(O)_p R^6$,
$(CH_2)_n NR^7C(O)NR^4R^5$,
$(CH_2)_n C(O)NR^4R^5$,
$(CH_2)_n NR^7C(O)R^6$,
$(CH_2)_n NR^7CO_2R^6$,
$O(CH_2)_n C(O)NR^4R^5$,
$CF_3$,
$CH_2CF_3$,
$OCF_3$, and
$OCH_2CF_3$;

in which phenyl, naphthyl, heteroaryl, cycloalkyl, and heterocyclyl are unsubstituted or substituted with one to three substituents independently selected from halogen, hydroxy, $C_{1-4}$ alkyl, trifluoromethyl, and $C_{1-4}$ alkoxy; and wherein any methylene ($CH_2$) carbon atom in $R^8$ is unsubstituted or substituted with one to two groups independently selected from halogen, hydroxy, and $C_{1-4}$ alkyl; or two substituents when on the same methylene ($CH_2$) group are taken together with the carbon atom to which they are attached to form a cyclopropyl group.

In one embodiment of the novel compounds of the present invention, m is 2.

In a second embodiment of the novel compounds of the present invention, m is 1.

In a third embodiment of the novel compounds of the present invention, X—Y is CH—O. In a class of this embodiment, Ar is phenyl unsubstituted or substituted with one to three $R^8$ substituents as defined above.

In a fourth embodiment of the novel compounds of the present invention, X—Y is CH—$S(O)_p$. In a class of this embodiment, Ar is phenyl unsubstituted or substituted with one to three $R^8$ substituents as defined above.

In a fifth embodiment of the novel compounds of the present invention, X—Y is CH—$NR^6$. In a class of this embodiment, Ar is phenyl unsubstituted or substituted with one to three $R^8$ substituents as defined above.

In a sixth embodiment of the novel compounds of the present invention, X—Y is CH—C(O). In a class of this embodiment, Ar is phenyl unsubstituted or substituted with one to three $R^8$ substituents as defined above In a seventh embodiment of the novel compounds of the present invention, X—Y is CH—$(CR^1R^2)_q$. In a class of this embodiment, q is 1 and Ar is phenyl unsubstituted or substituted with one to three $R^8$ substituents as defined above. In a class of this embodiment, q is 2 and Ar is phenyl unsubstituted or substituted with one to three $R^8$ substituents as defined above. In a third class of this embodiment, $R^1$ and $R^2$ are hydrogen and Ar is phenyl unsubstituted or substituted with one to three $R^8$ substituents.

In yet another embodiment of the novel compounds of the present invention, m is 2; X—Y is CH—O; and Ar is phenyl unsubstituted or substituted with one to three substituents independently selected from $R^8$ as defined above.

Illustrative, but nonlimiting examples, of novel compounds of the present invention that are useful as inhibitors of SCD are the following:

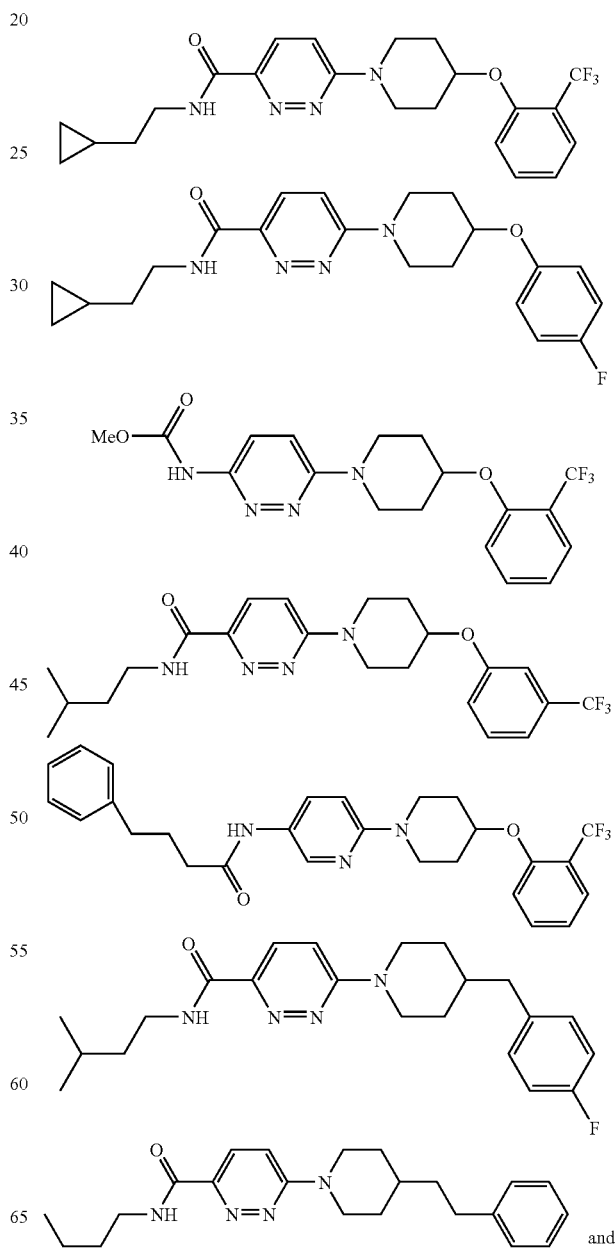

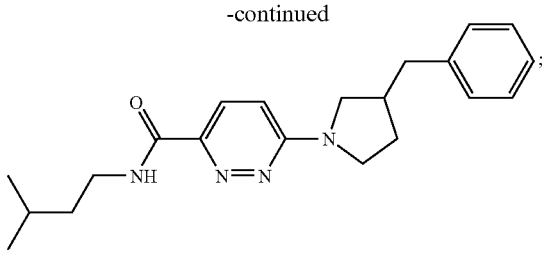

and pharmaceutically acceptable salts thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-6}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-6}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkylsulfinyl" refers to straight or branched chain alkylsulfoxides of the number of carbon atoms specified (e.g., $C_{1-6}$ alkylsulfinyl), or any number within this range [i.e., methylsulfinyl (MeSO—), ethylsulfinyl, isopropylsulfinyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heterocyclyl" refer to saturated or unsaturated non-aromatic rings or ring systems containing at least one heteroatom selected from O, S and N, further including the oxidized forms of sulfur, namely SO and $SO_2$. Examples of heterocycles include tetrahydrothiophene, tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

"Heteroaryl" means an aromatic or partially aromatic heterocycle that contains at least one ring heteroatom selected from O, S and N. Heteroaryls thus includes heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridinyl, 2-oxo-(1H)-pyridinyl (2-hydroxy-pyridinyl), 2-oxo-pyrrolidin-1-yl, oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, imidazo[4,5-b]pyridin-2-yl, imidazo[1,2-a]pyridinyl, [1,2,4-triazolo][4,3-a]pyridinyl, pyrazolo[1,5-a]pyridinyl, [1,2,4-triazolo][1,5-a]pyridinyl, 2-oxo-1,3-benzoxazolyl, 4-oxo-3H-quinazolinyl, 3-oxo-[1,2,4]-triazolo[4,3-a]-2H-pyridinyl, 5-oxo-[1,2,4]-4H-oxadiazolyl, 2-oxo-[1,3,4]-3H-oxadiazolyl, 2-oxo-1,3-dihydro-2H-imidazolyl, 3-oxo-2,4-dihydro-3H-1,2,4-triazolyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

Compounds of structural formula I may contain one or more asymmetric centers and can thus occur as racemates and racemic mixtures, single enantiomers, diastereomeric mixtures and individual diastereomers. The present invention is meant to comprehend all such isomeric forms of the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formula I may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetyl, pivaloyl, benzoyl, and aminoacyl, can be employed. Included are those esters and acyl groups known in the art for modifying the solubility or hydrolysis characteristics for use as sustained-release or prodrug formulations.

Solvates, in particular hydrates, of the compounds of structural formula I are included in the present invention as well.

The subject compounds are useful in a method of inhibiting the stearoyl-coenzyme A delta-9 desaturase enzyme (SCD) in a patient such as a mammal in need of such inhibition comprising the administration of an effective amount of the compound. The compounds of the present invention are therefore useful to control, prevent, and/or treat conditions and diseases mediated by high or abnormal SCD enzyme activity.

Thus, one aspect of the present invention concerns a method of treating hyperglycemia, diabetes or insulin resistance in a mammalian patient in need of such treatment, which comprises administering to said patient an effective amount of a compound in accordance with structural formula I or a pharmaceutically salt or solvate thereof.

A second aspect of the present invention concerns a method of treating non-insulin dependent diabetes mellitus (Type 2 diabetes) in a mammalian patient in need of such treatment comprising administering to the patient an antidiabetic effective amount of a compound in accordance with structural formula I.

A third aspect of the present invention concerns a method of treating obesity in a mammalian patient in need of such treatment comprising administering to said patient a compound in accordance with structural formula I in an amount that is effective to treat obesity.

A fourth aspect of the invention concerns a method of treating metabolic syndrome and its sequelae in a mammalian patient in need of such treatment comprising administering to said patient a compound in accordance with structural formula I in an amount that is effective to treat metabolic syndrome and its sequelae. The sequelae of the metabolic syndrome include hypertension, elevated blood glucose levels, high triglycerides, and low levels of HDL cholesterol.

A fifth aspect of the invention concerns a method of treating a lipid disorder selected from the group consisting of dyslipidemia, hyperlipidemia, hypertriglyceridemia, hypercholesterolemia, low HDL and high LDL in a mammalian patient in need of such treatment comprising administering to said patient a compound in accordance with structural formula I in an amount that is effective to treat said lipid disorder.

A sixth aspect of the invention concerns a method of treating atherosclerosis in a mammalian patient in need of such treatment comprising administering to said patient a compound in accordance with structural formula I in an amount effective to treat atherosclerosis.

A seventh aspect of the invention concerns a method of treating cancer in a mammalian patient in need of such treatment comprising administering to said patient a compound in accordance with structural formula I in an amount effective to treat cancer.

A further aspect of the invention concerns a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) fatty liver disease, (21) polycystic ovary syndrome, (22) sleep-disordered breathing, (23) metabolic syndrome, and

(24) other conditions and disorders where insulin resistance is a component, in a mammalian patient in need of such treatment comprising administering to the patient a compound in accordance with structural formula I in an amount that is effective to treat said condition.

Yet a further aspect of the invention concerns a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) fatty liver disease, (21) polycystic ovary syndrome, (22) sleep-disordered breathing, (23) metabolic syndrome, and (24) other conditions and disorders where insulin resistance is a component, and other conditions and disorders where insulin resistance is a component, in a mammalian patient in need of such treatment comprising administering to the patient a compound in accordance with structural formula I in an amount that is effective to delay the onset of said condition.

Yet a further aspect of the invention concerns a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) fatty liver disease, (21) polycystic ovary syndrome, (22) sleep-disordered breathing, (23) metabolic syndrome, and (24) other conditions and disorders where insulin resistance is a component, in a mammalian patient in need of such treatment comprising administering to the patient a compound in accordance with structural formula I in an amount that is effective to reduce the risk of developing said condition.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent, such as a mouse, species can be treated. However, the method can also be practiced in other species, such as avian species (e.g., chickens).

The present invention is further directed to a method for the manufacture of a medicament for inhibiting stearoyl-coenzyme A delta-9 desaturase enzyme activity in humans and animals comprising combining a compound of the present invention with a pharmaceutically acceptable carrier or diluent. More particularly, the present invention is directed to the use of a compound of structural formula I in the manufacture of a medicament for use in treating a condition selected from the group consisting of hyperglycemia, Type 2 diabetes, insulin resistance, obesity, and a lipid disorder in a mammal, wherein the lipid disorder is selected from the group consisting of dyslipidemia, hyperlipidemia, hypertriglyceridemia, hypercholesterolemia, low HDL, and high LDL.

The subject treated in the present methods is generally a mammal, preferably a human being, male or female, in whom inhibition of stearoyl-coenzyme A delta-9 desaturase enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of stearoyl-coenzyme A delta-9 desaturase (SCD) enzyme activity may be demonstrated by the following microsomal and whole-cell based assays:

I. SCD-Induced Rat Liver Microsome Assay:

The activity of compounds of formula I against the SCD enzyme is determined by following the conversion of radiolabeled-stearoyl-CoA to oleoyl-CoA using SCD1-induced rat liver microsome and a previously published procedure with some modifications (Joshi, et al., *J. Lipid Res.*, 18: 32-36 (1977)). After feeding wistar rats with a high carbohydrate/fat-free rodent diet (LabDiet # 5803, Purina) for 3 days, the SCD-induced livers were homogenized (1:10 w/v) in 250 mM sucrose, 1 mM EDTA, 5 mM DTT and 50 mM Tris-HCl (pH 7.5). After a 20 min centrifugation (18,000×g/4° C.) to remove tissue and cell debris, the microsome was prepared by a 100,000×g centrifugation (60 min) with the resulting pellet suspended in 100 mM sodium phosphate, 20% glycerol and 2 mM DTT. Test compound in 2 μL DMSO was incubated for 15 min at room temperature with 180 μL of the microsome (typically at about 100 μg/mL, in Tris-HCl buffer (100 mM, pH 7.5), ATP (5 mM), Coenzyme A (0.1 mM), Triton X-100 (0.5 mM) and NADH (2 mM)). The reaction was initiated by the addition of 20 μL of [$^3$H]-stearoyl-CoA (final concentration at 2 μM with the radioactivity concentration at 1 μCi/mL), and terminated by the addition of 150 μL of 1N sodium hydroxide. After 60 min at room temperature to hydrolyze the oleoyl-CoA and stearoyl-CoA, the solution was acidified by the addition of 150 μL of 15% phosphoric acid (v/v) in ethanol supplemented with 0.5 mg/mL stearic acid and 0.5 mg/mL oleic acid. [$^3$H]-oleic acid and [$^3$H]-stearic acid were then quantified on a HPLC that is equipped with a C-18 reverse phase column and a Packard Flow Scintillation Analyzer. Alternatively, the reaction mixture (80 μL) was mixed with a calcium chloride/charcoal aqueous suspension (100 μL of 15% (w/v) charcoal plus 20 μL of 2 N CaCl$_2$). The resulting mixture was centrifuged to precipitate the radioactive fatty acid species into a stable pellet. Tritiated water from SCD-catalyzed desaturation of 9,10-[$^3$H]-stearoyl-CoA was quantified by counting 50 μL of the supernant on a scintillation counter.

II. Whole Cell-Based SCD (Delta-9), Delta-5 and Delta-6 Desaturase Assays:

Human HepG2 cells were grown on 24-well plates in MEM media (Gibco cat# 11095-072) supplemented with 10% heat-inactivated fetal bovine serum at 37° C. under 5% $CO_2$ in a humidified incubator. Test compound dissolved in the media was incubated with the subconfluent cells for 15 min at 37° C. [1-$^{14}$C]-stearic acid was added to each well to a final concentration of 0.05 μCi/mL to detect SCD-catalyzed [$^{14}$C]-oleic acid formation. 0.05 μCi/m of [1-$^{14}$C]-eicosatrienoic acid or [1-$^{14}$C]-linolenic acid plus 10 μM of 2-amino-N-(3-chlorophenyl)benzamide (a delta-5 desaturase inhibitor) was used to index the delta-5 and delta-6 desaturase activities, respectively. After 4 h incubation at 37° C., the culture media was removed and the labeled cells were washed with PBS (3×1 mL) at room temperature. The labeled cellular lipids were hydrolyzed under nitrogen at 65° C. for 1 h using 400 μL of 2N sodium hydroxide plus 50 μL of L-α-phosphatidylcholine (2 mg/mL in isopropanol, Sigma #P-3556). After acidification with phosphoric acid (60 μL), the radioactive species were extracted with 300 μL of acetonitrile and quantified on a HPLC that was equipped with a C-18 reverse phase column and a Packard Flow Scintillation Analyzer. The levels of [$^{14}$C]-oleic acid over [$^{14}$C]-stearic acid, [$^{14}$C]-arachidonic acid over [$^{14}$C]-eicosatrienoic acid, and [$^{14}$C]-eicosatetraenoic acid (8,11,14,17) over [$^{14}$C]-linolenic acid were used as the corresponding activity indices of SCD, delta-5 and delta-6 desaturase, respectively.

The SCD inhibitors of formula I generally exhibit an inhibition constant $IC_{50}$ of less than 1 μM and more typically less than 0.1 μM. Generally, the $IC_{50}$ ratio for delta-5 or delta-6 desaturases to SCD for a compound of formula I is at least about ten or more, and preferably about hundred or more.

In Vivo Efficacy of Compounds of the Present Invention:

The in vivo efficacy of compounds of formula I was determined by following the conversion of [1-$^{14}$C]-stearic acid to [1-$^{14}$C]oleic acid in animals as exemplified below. Mice were dosed with a compound of formula I and one hour later the radioactive tracer, [1-$^{14}$C]-stearic acid, was dosed at 20 μCi/kg IV. At 3 h post dosing of the compound, the liver was harvested and then hydrolyzed in 10 N sodium hydroxide for 24 h at 80° C., to obtain the total liver fatty acid pool. After phosphoric acid acidification of the extract, the amount of [1-$^{14}$C]-stearic acid and [1-$^{14}$C]-oleic acid was quantified on a HPLC that was equipped with a C-18 reverse phase column and a Packard Flow Scintillation Analyzer.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of formula I, and either administered separately or in the same pharmaceutical composition, include, but are not limited to:

(a) dipeptidyl peptidase IV (DPP-IV) inhibitors;

(b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, Galida, TAK-559, PPARα agonists, such as fenofibric acid derivatives (gemfibrozil, clofibrate, fenofibrate and bezafibrate), and selective PPARγ modulators (SPPARγM's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide, glyburide, glipizide, glimepiride, and meglitinides, such as nateglinide and repaglinide;

(e) α-glucosidase inhibitors (such as acarbose and miglitol);

(f) glucagon receptor antagonists, such as those disclosed in WO 98/04528, WO 99/01423, WO 00/39088, and WO 00/69810;

(g) GLP-1, GLP-1 analogues or mimetics, and GLP-1 receptor agonists, such as exendin-4 (exenatide), liraglutide (N,N-2211), CJC-1131, LY-307161, and those disclosed in WO 00/42026 and WO 00/59887;

(h) GIP and GIP mimetics, such as those disclosed in WO 00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA:cholesterol acyltransferase inhibitors, such as avasimibe, and (viii) antioxidants, such as probucol;

(k) PPARδ agonists, such as those disclosed in WO 97/28149;

(l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, $β_3$ adrenergic receptor agonists, melanocortin-receptor agonists, in particular melanocortin-4 receptor agonists, ghrelin antagonists, bombesin receptor agonists (such as bombesin receptor subtype-3 agonists), and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(o) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;

(p) glucokinase activators (GKAs), such as those disclosed in WO 03/015774; WO 04/076420; and WO 04/081001;

(q) inhibitors of 11β-hydroxysteroid dehydrogenase type 1, such as those disclosed in U.S. Pat. No. 6,730,690; WO 03/104207; and WO 04/058741;

(r) inhibitors of cholesteryl ester transfer protein (CETP), such as torcetrapib; and (s) inhibitors of fructose 1,6-bisphosphatase, such as those disclosed in U.S. Pat. Nos. 6,054,587; 6,110,903; 6,284,748; 6,399,782; and 6,489,476.

Dipeptidyl peptidase-IV inhibitors that can be combined with compounds of structural formula I include those disclosed in U.S. Pat. No. 6,699,871; WO 02/076450 (3 Oct. 2002); WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); WO 03/082817 (9 Oct. 2003); WO 03/000181 (3 Jan. 2003); WO 04/007468 (22 Jan. 2004); WO 04/032836 (24 Apr. 2004); WO 04/037169 (6 May 2004); and WO 04/043940 (27 May 2004). Specific DPP-IV inhibitor compounds include isoleucine thiazolidine (P32/98); NVP-DPP-728; LAF 237; P93/01; and saxagliptin (BMS 477118).

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, bombesin receptor agonists, and melanin-concentrating hormone (MCH) receptor antagonists. For a review of antiobesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs,"*Expert Opin. Emerging Drugs*, 8: 217-237 (2003); and J. A. Fernandez-Lopez, et al., "Pharmacological Approaches for the Treatment of Obesity," *Drugs*, 62: 915-944 (2002).

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; U.S. Pat. No. 5,292,736; PCT Publication WO 03/086288; PCT Publication WO 03/087037; PCT Publication WO 04/048317; PCT Publication WO 03/007887; PCT Publication WO 03/063781; PCT Publication WO 03/075660; PCT Publication WO 03/077847; PCT Publication WO 03/082190; PCT Publication WO 03/082191; PCT Publication WO 03/087037; PCT Publication WO 03/086288; PCT Publication WO 04/012671; PCT Publication WO 04/029204; PCT Publication WO 04/040040; PCT Publication WO 01/64632; PCT Publication WO 01/64633; and PCT Publication WO 01/64634.

Melanocortin-4 receptor (MC4R) agonists useful in the present invention include, but are not limited to, those disclosed in U.S. Pat. No. 6,294,534, U.S. Pat. Nos. 6,350,760, 6,376,509, 6,410,548, 6,458,790, U.S. Pat. No. 6,472,398, U.S. Pat. No. 5,837,521, U.S. Pat. No. 6,699,873, which are hereby incorporated by reference in their entirety; in US Patent Application Publication Nos. US 2002/0004512, US2002/0019523, US2002/0137664, US2003/0236262, US2003/0225060, US2003/0092732, US2003/109556, US 2002/0177151, US 2002/187932, US 2003/0113263, which are hereby incorporated by reference in their entirety; and in WO 99/64002, WO 00/74679, WO 02/15909, WO 01/70708, WO 01/70337, WO 01/91752, WO 02/068387, WO 02/068388, WO 02/067869, WO 03/007949, WO 2004/024720, WO 2004/089307, WO 2004/078716, WO 2004/078717, WO 2004/037797, WO 01/58891, WO 02/070511, WO 02/079146, WO 03/009847, WO 03/057671, WO 03/068738, WO 03/092690, WO 02/059095, WO 02/059107, WO 02/059108, WO 02/059117, WO 02/085925, WO 03/004480, WO 03/009850, WO 03/013571, WO 03/031410, WO 03/053927, WO 03/061660, WO 03/066597, WO 03/094918, WO 03/099818, WO 04/037797, WO 04/048345, WO 02/018327, WO 02/080896, WO 02/081443, WO 03/066587, WO 03/066597, WO 03/099818, WO 02/062766, WO 03/000663, WO 03/000666, WO 03/003977, WO 03/040107, WO 03/040117, WO 03/040118, WO 03/013509, WO 03/057671, WO 02/079753, WO 02/092566, WO 03/-093234, WO 03/095474, and WO 03/104761.

One particular aspect of combination therapy concerns a method of treating a condition selected from the group consisting of hypercholesterolemia, atherosclerosis, low HDL levels, high LDL levels, hyperlipidemia, hypertriglyceridemia, and dyslipidemia, in a mammalian patient in need of such treatment comprising administering to the patient a therapeutically effective amount of a compound of structural formula I and an HMG-CoA reductase inhibitor.

More particularly, this aspect of combination therapy concerns a method of treating a condition selected from the group consisting of hypercholesterolemia, atherosclerosis, low HDL levels, high LDL levels, hyperlipidemia, hypertriglyceridemia and dyslipidemia in a mammalian patient in need of such treatment wherein the HMG-CoA reductase inhibitor is a statin selected from the group consisting of lovastatin, simvastatin, pravastatin, cerivastatin, fluvastatin, atorvastatin, and rosuvastatin.

In another aspect of the invention, a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions is disclosed comprising administering to a mammalian patient in need of such treatment a therapeutically effective amount of a compound of structural formula I and an HMG-CoA reductase inhibitor.

In another aspect of the invention, a method for delaying the onset or reducing the risk of developing atherosclerosis in a human patient in need of such treatment is disclosed comprising administering to said patient an effective amount of a compound of structural formula I and an HMG-CoA reductase inhibitor.

More particularly, a method for delaying the onset or reducing the risk of developing atherosclerosis in a human patient in need of such treatment is disclosed, wherein the HMG-CoA reductase inhibitor is a statin selected from the group consisting of: lovastatin, simvastatin, pravastatin, cerivastatin, fluvastatin, atorvastatin, and rosuvastatin.

In another aspect of the invention, a method for delaying the onset or reducing the risk of developing atherosclerosis in a human patient in need of such treatment is disclosed, wherein the HMG-Co A reductase inhibitor is a statin and further comprising administering a cholesterol absorption inhibitor.

More particularly, in another aspect of the invention, a method for delaying the onset or reducing the risk of developing atherosclerosis in a human patient in need of such treatment is disclosed, wherein the HMG-Co A reductase inhibitor is a statin and the cholesterol absorption inhibitor is ezetimibe.

In another aspect of the invention, a pharmaceutical composition is disclosed which comprises:

(1) a compound of structural formula I;

(2) a compound selected from the group consisting of:

(a) dipeptidyl peptidase IV (DPP-IV) inhibitors;

(b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, Galida, TAK-559, PPARα agonists, such as fenofibric acid derivatives (gemfibrozil, clofibrate, fenofibrate and bezafibrate), and selective PPARγ modulators (SPPARγM's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide, glyburide, glipizide, glimepiride, and meglitinides, such as nateglinide and repaglinide;

(e) α-glucosidase inhibitors (such as acarbose and miglitol);

(f) glucagon receptor antagonists, such as those disclosed in WO 98/04528, WO 99/01423, WO 00/39088, and WO 00/69810;

(g) GLP-1, GLP-1 analogues or mimetics, and GLP-1 receptor agonists, such as exendin-4 (exenatide), liraglutide (N,N-2211), CJC-1131, LY-307161, and those disclosed in WO 00/42026 and WO 00/59887;

(h) GIP and GIP mimetics, such as those disclosed in WO 00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA:cholesterol acyltransferase inhibitors, such as avasimibe, and (viii) antioxidants, such as probucol;

(k) PPARδ agonists, such as those disclosed in WO 97/28149;

(l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, $β_3$ adrenergic receptor agonists, melanocortin-receptor agonists, in particular melanocortin-4 receptor agonists, ghrelin antagonists, bombesin receptor agonists (such as bombesin receptor subtype-3 agonists), and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(o) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;

(p) glucokinase activators (GKAs), such as those disclosed in WO 03/015774; WO 04/076420; and WO 04/081001;

(q) inhibitors of 11β-hydroxysteroid dehydrogenase type 1, such as those disclosed in U.S. Pat. No. 6,730,690; WO 03/104207; and WO 04/058741;

(r) inhibitors of cholesteryl ester transfer protein (CETP), such as torcetrapib; and (s) inhibitors of fructose 1,6-bisphosphatase, such as those disclosed in U.S. Pat. Nos. 6,054,587; 6,110,903; 6,284,748; 6,399,782; and 6,489,476; and (3) a pharmaceutically acceptable carrier.

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of stearoyl-CoA delta-9 desaturase enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Preparation of Compounds of the Invention:

The compounds of structural formula I can be prepared according to the procedures of the following Schemes and Examples, using appropriate materials and are further exemplified by the following specific examples. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted. Mass spectra (MS) were measured by electrospray ion-mass spectroscopy (ESI) or atmospheric pressure chemical ionization (APCI).

| List of Abbreviations: | |
|---|---|
| Alk = | alkyl |
| APCI = | atmospheric pressure chemical ionization |
| Ar = | aryl |
| Boc = | tert-butoxycarbonyl |
| br = | broad |
| $CH_2Cl_2$= | dichloromethane |
| $CH_2N_2$= | diazomethane |
| d = | doublet |
| DBU = | 1,8-diazabicyclo[5.4.0]undec-7-ene |
| DAST = | diethylaminosulfur trifluoride |
| Deoxofluor ® = | bis(2-methoxyethyl)aminosulfur trifluoride |
| DIBAL-H = | diisobutylaluminum hydride |
| DMF = | dimethylformamide |
| DMSO = | dimethyl sulfoxide |
| ESI = | electrospray ionization |
| EtOAc = | ethyl acetate |
| HATU = | o-(7-azabenzotriazol-1-y1)-N,N,N',N'-tetramethyluronium hexafluorophosphate |
| HOAc = | acetic acid |
| KOH = | potassium hydroxide |
| LiOH = | lithium hydroxide |
| m = | multiplet |
| m-CPBA = | 3-chloroperoxybenzoic acid |
| MeOH = | methyl alcohol |
| $MgSO_4$= | magnesium sulfate |
| MS = | mass spectroscopy |
| NaHMDS = | sodium bis(trimethylsilyl)amide |
| NaOH = | sodium hydroxide |
| $Na_2SO_4$= | sodium sulfate |
| $NH_4OAc$ = | ammonium acetate |
| NMP = | N-methylpyrrolidinone |
| NMR = | nuclear magnetic resonance spectroscopy |
| PG = | protecting group |
| pTSA = | p-toluenesulfonic acid |
| rt = | room temperature |
| s = | singlet |
| t = | triplet |
| THF = | tetrahydrofuran |
| TFA = | trifluoroacetic acid |
| TFAA = | trifluoroacetic anhydride |
| TsCl = | tosyl chloride |
| TsOH = | toluene-4-sulfonic acid |

Method A:

A halo-substituted pyridazine such as represented by 1 is reacted with an appropriately substituted amine 2 in the presence of a base such as DBU, alkali metal (K, Na, Cs) carbonate in a solvent such as THF, 1,4-dioxane or DMF at a temperature range of room temperature to refluxing to give the desired product 3.

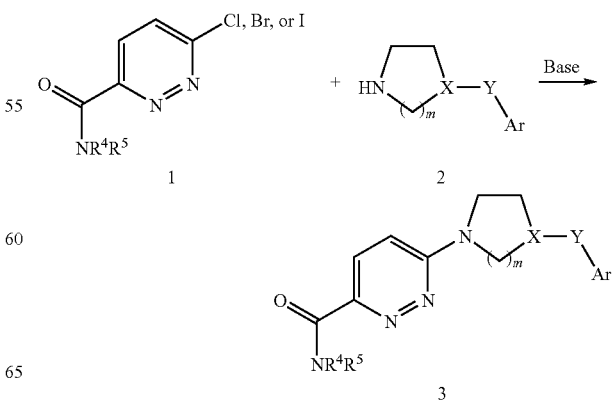

Method B:

A halo-substituted pyridazine 4 is reacted with an appropriately substituted amine 2 in the presence of a base such as DBU, alkali metal (K, Na, Cs) carbonate in a solvent such as DMF at a temperature range of room temperature to refluxing to provide an ester intermediate. Saponification then gives the carboxylic acid 5. Treatment of acid 5 with diphenylphosphoryl azide in the presence of an appropriate alcohol in a solvent such as DMF at 60-100° C. gives the desired product 6.

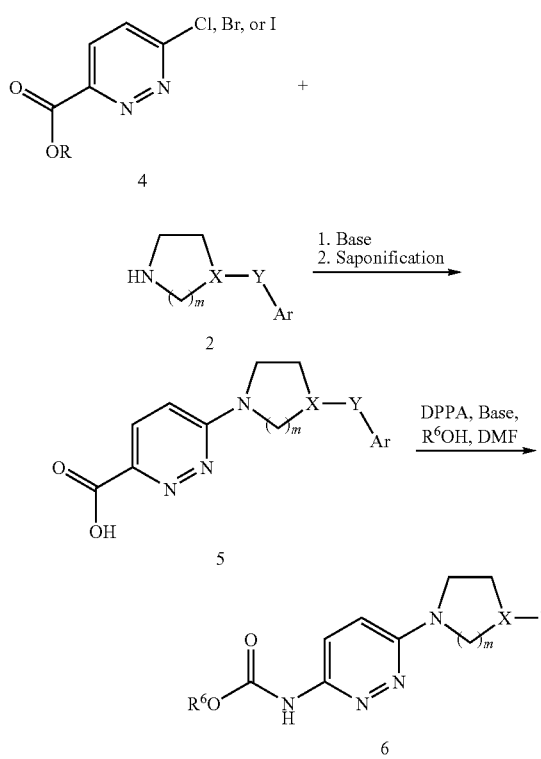

Method C:

A halo-substituted pyridazine 7 is reacted with an appropriately substituted amine 2 in the presence of a base such as DBU, alkali metal (K, Na, Cs) carbonate in a solvent such as DMF at a temperature range of room temperature to refluxing to provide a coupling intermediate 8. Displacement with a thiol in the presence of a base in DMF at a temperature range of room temperature to refluxing provides 9. Oxidation with mCPBA or hydrogen peroxide gives the desired sulfone 10.

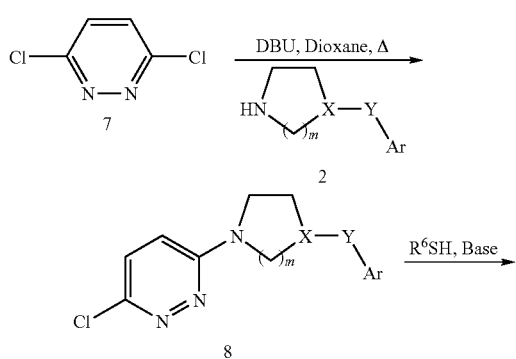

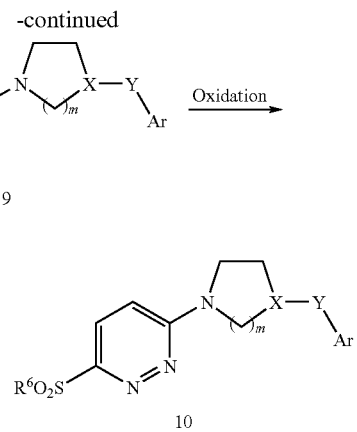

Method D:

Compound 11, prepared according to Method C, is oxidized to the corresponding sulfoxide 12, which is converted to the sulfonamide 13 following the reported procedure (*Synlett.* 1997, 4, 375-377).

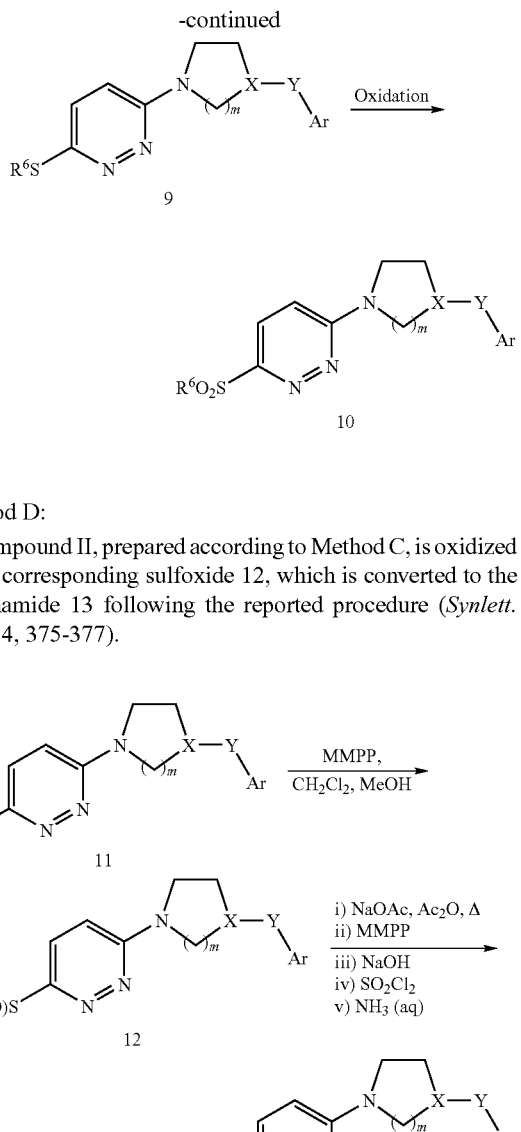

Method E:

Intermediate 8 from Method C is reacted with an alcohol in the presence of a base at a temperature range of room temperature to refluxing to provide the desired displacement product 14.

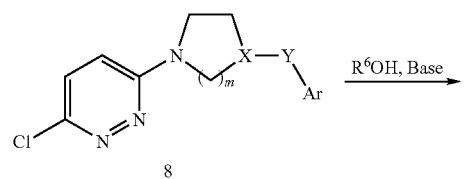

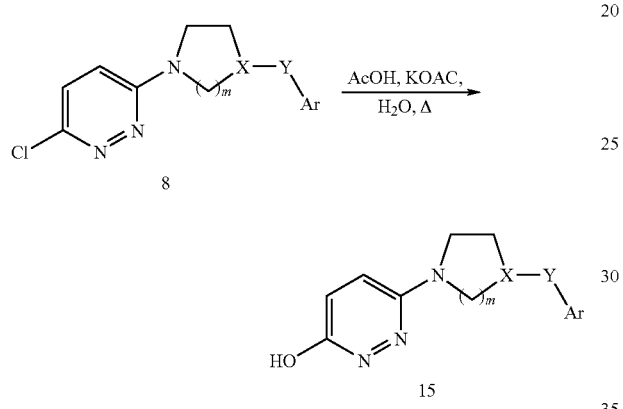

14

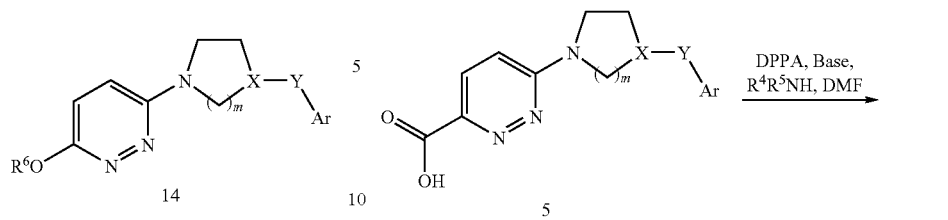

5

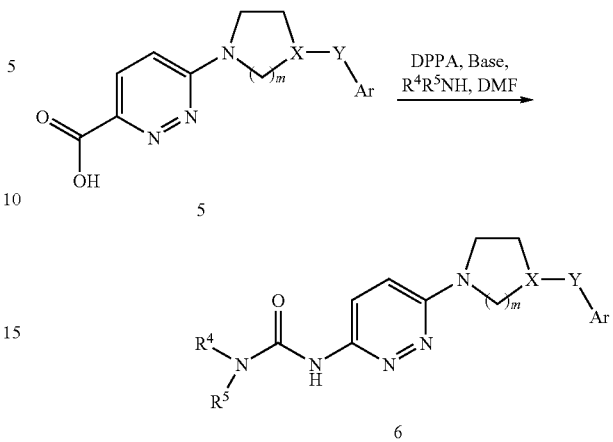

6

Method F:

Intermediate 8 from Method C is heated with potassium acetate in acetic acid to provide the desired displacement product 15.

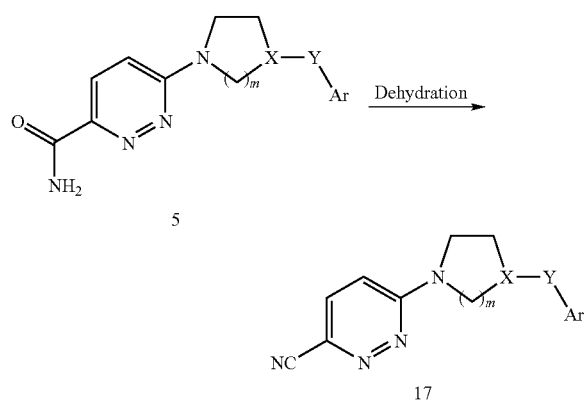

15

Method G:

Amide 16 is converted to the nitrile 17 under a suitable dehydrating condition such as TFAA and pyridine in dioxane or trifluoromethanesulfonic anhydride and triethylamine in CH$_2$Cl$_2$.

Method I:

A halo-substituted pyridine such as represented by 18 is reacted with an appropriately substituted amine 2 in the presence of a base such as DBU, alkali metal (K, Na, Cs) carbonate in a solvent such as THF, 1,4-dioxane or DMF at a temperature range of room temperature to refluxing to give the desired product 19.

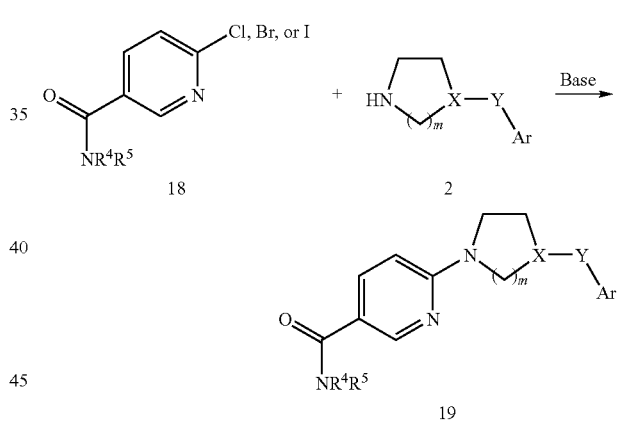

Method H:

Treatment of acid 5 from Method B with diphenylphosphoryl azide in the presence of an appropriate amine in a solvent such as DMF at 60-100° C. gives the desired product 17.

Method J:

A halo-substituted nitro-pyridine 20 is reacted with an appropriately substituted amine 2 in the presence of a base such as DBU, alkali metal (K, Na, Cs) carbonate in a solvent such as DMF at a temperature range of room temperature to refluxing to provide intermediate 21. The nitro group is reduced with hydrogen in the presence of 10% Pd/C to give the amino intermediate 22. Coupling reaction with an acyl halide then gives the desired product 23.

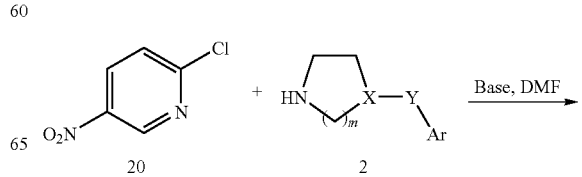

29

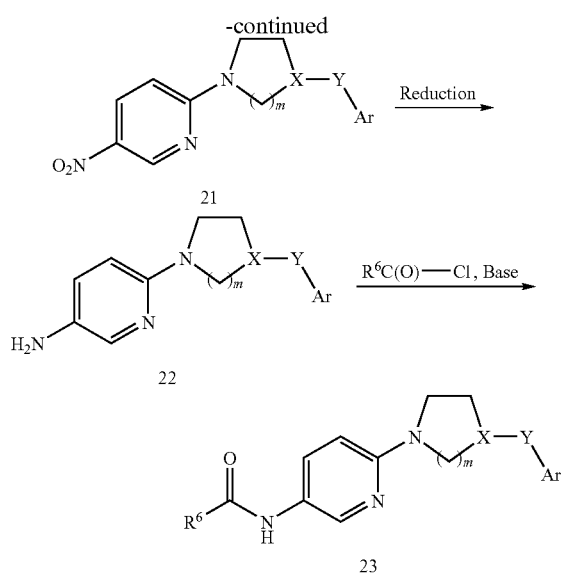

Method K:

Intermediate 22 from Method J is reacted with a chloroformate to give the desired product 24.

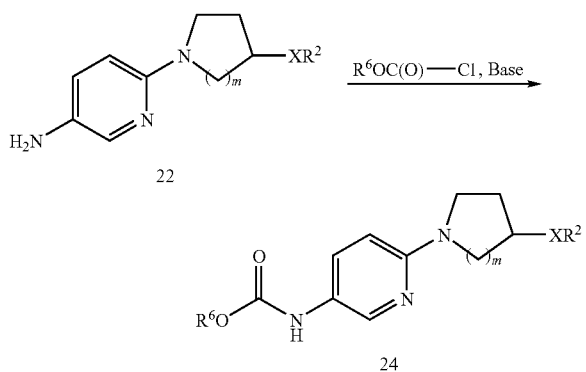

Method L:

Intermediate 22 from Method J is reacted with an isocyanate to give the desired product 25.

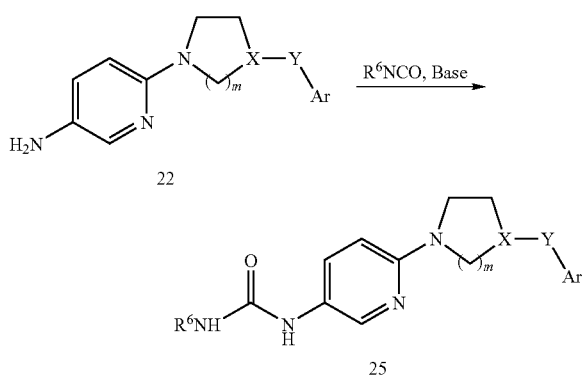

30

The following Examples are provided to illustrate the invention and are not to be construed as limiting the scope of the invention in any manner.

Preparation of Intermediates:

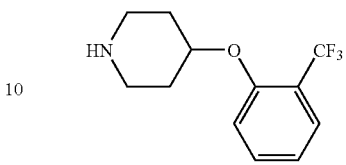

4-[2-(Trifluoromethyl)phenoxy]piperidine

To a solution of Boc-4-hydroxy-1-piperidine (25 g, 124 mmol), 2-hydroxy-benzotrifluoride (22 g, 136 mmol) and triphenylphosphine (39 g, 149 mmol) in THF was added diethyl azodicarboxylate dropwise (23.5 mL, 149 mmol) at 0° C. The mixture was then warmed to room temperature and stirred for 14 h. The mixture was concentrated and diluted with ethyl ether, washed with 1N NaOH, water then dried over $Na_2SO_4$. The mixture was concentrated and diluted with $Et_2O$/hexanes 35:65, the precipitated phosphine oxide was filtered, and the filtrate purified by silica gel chromatography using $Et_2O$/hexanes 35:65 as eluent to give 1-piperidinecarboxylic acid, 4-[2-(trifluoromethyl)phenoxy]-1,1-dimethylethyl ester as a solid. Trifluoroacetic acid (26.3 mL, 342 mmol) was added to a solution of 1-piperidinecarboxylic acid, 4-[2-(trifluoromethyl)phenoxy]-1,1-dimethylethyl ester (29.5 g, 85 mmol) in $CH_2Cl_2$ (171 mL). The mixture was stirred at room temperature for 16 h. The solvent was evaporated and diluted with EtOAc (200 mL), washed with NaOH (3×100 mL, 2N), brine, dried over $Na_2SO_4$, and evaporated to give the title compound as an oil. $^1H$ NMR (500 MHz, $CDCl_3$): δ 1.77-1.84 (m, 2H), 1.97-2.03 (m, 2H), 2.75-2.81 (m, 2H), 3.14-3.20 (m, 2H), 4.56-4.60 (m, 1H), 6.98-7.02 (m, 2H), 7.47 (t, 1H), 7.59 (d, 1H).

EXAMPLE 1

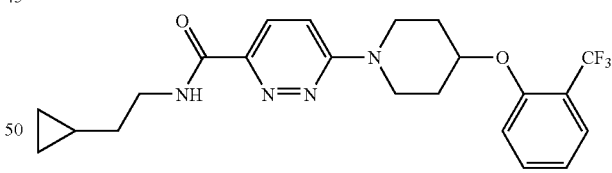

N-(2-Cyclopropylethyl)-6-{4-[2-(trifluoromethyl) phenoxy]piperidin-1-yl}pyridazine-3-carboxamide Step 1: 6-Chloropyridazine-3-carboxylic acid To concentrated sulfuric acid (175 mL) in a flask equipped with a mechanical stirrer was added 3-chloro-6-methylpyridazine (25 g, 194 mmol). To the resulting solution was added $K_2Cr_2O_7$ (69 g, 234 mmol) portionwise over 40 min, using a cold water bath to maintain the internal temperature below 65° C. The reaction was then maintained at 60° C. for 3 h. The mixture was cooled and quenched by the addition of ice, then poured onto 200 g ice and extracted eight times with EtOAc. The combined organic layers were washed with brine, dried over MgSO$_4$ and evaporated to give the title compound.

Step 2: 6-Chloro-N-(2-cyclopropylethyl)pyridazine-3-carboxamide

To a suspension of 6-chloropyridazine-3-carboxylic acid (4.1 g, 25.8 mmol) from Step 1 and DMF (50 μL) in CH$_2$Cl$_2$ (60 mL) at r.t. was added oxalyl chloride (5.0 mL, 57.1 mmol) and the mixture was refluxed for 30 min. Volatile materials were removed in vacuo to give the crude acid chloride as a pale yellow solid. The acid chloride was dissolved in CH$_2$Cl$_2$ (40 mL) and added to a solution of cyclopropylethylamine (2.4 g, 28.2 mmol) and Et$_3$N (11 mL, 78 mmol) in CH$_2$Cl$_2$ at 0° C. over a period of about 15 min. After further stirring for 30 min, the mixture was diluted with more CH$_2$Cl$_2$, washed successively with 10% HCl, saturated aqueous NaHCO$_3$, water, dried (Na$_2$SO$_4$) and concentrated. Chromatography over silica gel and elution with hexanes-EtOAc (2:1) gave the title compound as a white powder. $^1$H NMR (500 MHz, Acetone-d$_6$): δ 0.12 (d, 2H), 0.47 (t, 2H), 0.80 (s, 1H), 1.57-1.61 (m, 2H), 3.58-3.62 (m, 2H), 8.02 (d, 1H), 8.31 (d, 1H), 8.62 (s, 1H).

Step 3: N-(2-Cyclopropylethyl)-6-{4-[2-(trifluoromethyl)phenoxy]piperidin-1-yl}pyridazine-3-carboxamide A mixture of 6-chloro-N-(2-cyclopropylethyl)pyridazine-3-carboxamide (180 mg, 0.73 mmol), 4-[2-(trifluoromethyl)phenoxy]piperidine (150 mg, 0.67 mmol), potassium carbonate (184 mg, 1.33 mmol) and tetrabutylammonium iodide (7 mg, 0.02 mmol) in dioxane (10 mL) was refluxed for 2 days. After cooling, the mixture was diluted with EtOAc and filtered through celite. Solvent was removed in vacuo. Combi-Flash chromatography (10 g, 50-80% EtOAc in hexanes in 20 min, 20 mL/min, 18 mL/fraction) gave the title compound as a white powder. $^1$H NMR (500 MHz, acetone-d$_6$): δ 0.11-0.13 (m, 2H), 0.45-0.49 (m, 2H), 0.76-0.84 (m, 1H), 1.56 (q, 2H), 2.13-2.20 (m, 4H), 3.52-3.56 (m, 2H), 3.91-3.97 (m, 2H), 4.00-4.06 (m, 2H), 5.01-5.05 (m, 1H), 7.12 (t, 1H), 7.37 (m, 2H), 7.61-7.67 (m, 2H), 7.92 (d, 1H), 8.24 (s, 1H); MS (+ESI) m/z 435 (MH$^+$).

EXAMPLE 2

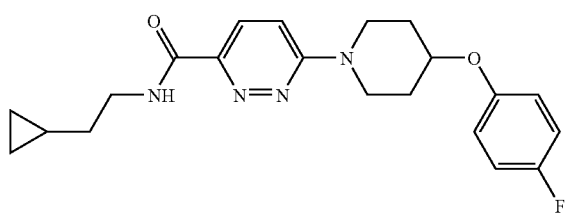

N-(2-Cyclopropylethyl)-6-[4-(4-fluorophenoxy)piperidin-1-yl]pyridazine-3-carboxamide The title compound was prepared in the same manner as described for Example 1, step 3 from 6-chloro-N-(2-cyclopropylethyl)pyridazine-3-carboxamide and 4-(4-fluorophenoxy)piperidine. $^1$H NMR (500 MHz, acetone-d$_6$): δ 0.11-0.13 (m, 2H), 0.45-0.49 (m, 2H), 0.76-0.84 (m, 1H), 1.56 (q, 2H), 1.78-1.85 (m, 2H), 2.08-2.16 (m, 2H), 3.54 (q, 2H), 3.70-3.76 (m, 2H), 4.16-4.22 (m, 2H), 4.69-4.75 (m, 1H), 7.05-7.11 (m, 4H), 7.34 (d, 1H), 7.91 (d, 1H), 8.24 (s, 1H); MS (+ESI) m/z 385 (MH$^+$).

EXAMPLE 3

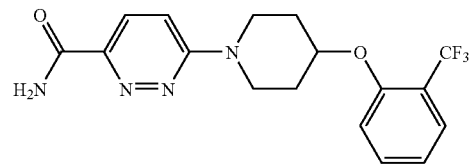

6-{4-[2-(Trifluoromethyl)phenoxy]piperidin-1-yl}pyridazine-3-carboxamide

Step 1: Methyl 6-chloropyridazine-3-carboxylate

To a suspension of 6-chloropyridazine-3-carboxylic acid (4.2 g, 26.5 mmol) in a mixture of dichloromethane (100 mL) and ethyl acetate (30 mL) and a few drops of DMF was added oxalyl chloride (3 mL, 34 mmol). The mixture was stirred at room temperature for 4 h until solution was attained, then quenched with 20 mL of methanol. After 15 min, the mixture was concentrated, and the resulting solid was swirled in ether and filtered. The solid was triturated with dichloromethane and the filtrate was evaporated to provide the title compound. $^1$H NMR (400 MHz, acetone-d$_6$): δ 4.04 (s, 3H), 8.05 (d, 1H), 8.31 (d, 1H).

Step 2: Methyl 6-{4-[2-(trifluoromethyl)phenoxy]piperidin-1-yl}pyridazine-3-carboxylate A mixture of methyl 6-chloropyridazine-3-carboxylate (500 mg, 0.2.9 mmol), 4-[2-(trifluoromethyl)phenoxy]piperidine (851 mg, 0.3.5 mmol), potassium carbonate (802 mg, 5.8 mmol) and tetrabutylammonium iodide (20 mg, 0.06 mmol) in dioxane (30 mL) was refluxed for 24 h. After cooling, the mixture was filtered through celite, washed with EtOAc and concentrated. CombiFlash chromatography (40 g, 60-90% EtOAc in hexanes in 20 min, 35 mL/min, 18 mL/fraction) gave the title compound as a white solid. $^1$H NMR (400 MHz, acetone-d$_6$): δ 1.93-1.99 (m, 2H), 2.14-2.20 (m, 2H), 3.93 (s, 3H), 3.97-4.09 (m, 4H), 5.03-5.07 (m, 1H), 7.13 (t, 1H), 7.31 (d, 1H), 7.40 (d, 1H), 7.65 (dd, 2H), 7.89 (d, 1H).

Step 3: 6-{4-[2-(Trifluoromethyl)phenoxy]piperidin-1-yl}pyridazine-3-carboxylic acid A mixture of methyl 6-{4-[2-(trifluoromethyl)phenoxy]piperidin-1-yl}pyridazine-3-carboxylate (800 mg, 2.1 mmol) and lithium hydroxide monohydrate (352 mg, 8.4 mmol) in THF (10 mL) and water (5 mL) was stirred at r.t. overnight, then acidified with 1M aqueous HCl (9 mL). Volatile materials were removed in vacuo. The residue was diluted with water and extracted with EtOAc. The organic extract was washed with diluted brine, dried (Na$_2$SO$_4$), concentrated and swished with Et$_2$O to give the title compound as a white powder. $^1$H NMR (400 MHz, acetone-d$_6$): δ 1.97 (m, 2H), 2.15-2.21 (m, 2H), 4.00-4.10 (m, 4H), 5.04-5.08 (m, 1H), 7.13 (t, 1H), 7.39 (m, 2H), 7.63-7.69 (m, 2H), 7.94 (d, 1H).

Step 4: 6-{4-[2-(Trifluoromethyl)phenoxy]piperidin-1-yl}pyridazine-3-carboxamide To a mixture of 6-{4-[2-(trifluoromethyl)phenoxy]piperidin-1-yl}pyridazine-3-carboxylic acid (250 mg, 0.7 mmol), HOBt (92 mg, 0.7 mmol), HATU (518 mg, 1.4 mmol) and ammonium chloride (74 mg, 1.4 mmol) in DMF (5 mL) was added N,N-diisopropylethylamine (592 µL, 3.4 mmol) at room temperature. The mixture was stirred at room temperature overnight, diluted with water and extracted with EtOAc. The organic extract was washed twice with 1N NaOH, brine, dried (Na$_2$SO$_4$) and concentrated. CombiFlash chromatography (10 g, 80-100% EtOAc in hexanes, 20 mL/min, 18 mL/fraction) gave the title compound as a white powder. $^1$H NMR (400 MHz, acetone-d$_6$): δ 1.93-1.99 (m, 2H), 2.14-2.20 (m, 2H), 3.93-4.09 (m, 4H), 5.05 (s, 1H), 6.72 (s, 1H), 7.13 (t, 1H), 7.38 (m, 2H), 7.62-7.68 (m, 2H), 7.84 (s, 1H), 7.94 (d, 1H). MS (+ESI) m/z 367 (MH$^+$).

EXAMPLE 4

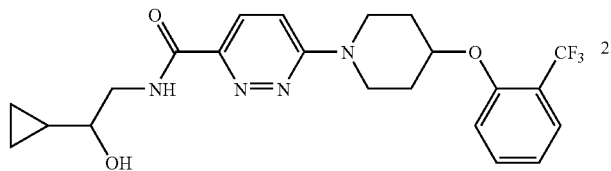

N-(2-Cyclopropyl-2-hydroxyethyl)-6-{4-[2-(trifluoromethyl)phenoxy]piperidin-1-yl}pyridazine-3-carboxamide

Step 1: 1-Cyclopropyl-2-nitroethanol

To a solution of cyclopropanecarbaldehyde (1.4 g, 20 mmol) and nitromethane (1.2 g, 20 mmol) in MeOH at 0° C. was added a solution of NaOH (840 mmol, 21 mmol) in water (8 mL). The mixture was stirred at room temperature for 1 h and then HOAc (1.3 mL) was added. Volatile solvent was removed in vacuo. The residue was diluted with water and extracted twice with EtOAc. The combined EtOAc extracted was washed with brine, dried (Na$_2$SO$_4$) and concentrated to give the title compound as a yellow liquid.

Step 2: 2-Amino-1-cyclopropylethanol

To a suspension of LAH (2 g, 53 mmol) in ether (60 mL) at 0° C. was added a solution of 1-cyclopropyl-2-nitroethanol (2.1 g, 16 mmol) in ether over 15 min. The mixture was stirred at r.t. for 30 min and then heated to refluxing for 3 h. After cooling to 0° C., the mixture was quenched with 2-propanol (20 mL), followed by saturated aqueous NaCl (7 mL), further stirred for 30 min and filtered through celite. The filter cake was washed with 2-propanol:ether (1:3). The combined filtrates were concentrated to give crude title compound as a light brown oil.

Step 3: N-(2-Cyclopropyl-2-hydroxyethyl)-6-{4-[2-(trifluoromethy)phenoxy]piperidin-1-yl}pyridazine-3-carboxamide To a mixture of 6-{4-[2-(trifluoromethyl)phenoxy]piperidin-1-yl}pyridazine-3-carboxylic acid (120 mg, 0.3 mmol), 2-amino-1-cyclopropylethanol (57 mg, 0.56 mmol) and HATU (249 mg, 0.65 mmol) in DMF (4 mL) was added N,N-diisopropylethylamine (285 µL, 3.4 mmol) at room temperature. The mixture was stirred at room temperature for 4 h, diluted with water and extracted with EtOAc. The EtOAc extract was washed with water, diluted twice with brine, dried (Na$_2$SO$_4$) and concentrated. CombiFlash chromatography (10 g, 90-100% EtOAc in hexanes in 20 min, 20 mL/min, 18 mL/fraction) gave the title compound as a light brown foam. $^1$H NMR (400 MHz, acetone-d$_6$): δ 0.30-0.52 (m, 4H), 0.93-1.01 (m, 1H), 1.92-2.00 (m, 2H), 2.14-2.24 (m, 2H), 3.22-3.28 (m, 1H), 3.43-3.49 (m, 1H), 3.71-3.77 (m, 1H), 3.94-4.08 (m, 4H), 4.24 (d, 1H), 5.04 (m, 1H), 7.13 (t, 1H), 7.38 (m, 2H), 7.62-7.68 (m, 2H), 7.94 (d, 1H), 8.35 (s, 1H). MS (+ESI) m/z 451 (MH$^+$).

EXAMPLE 5

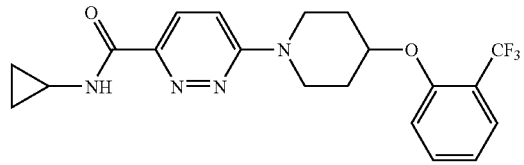

N-Cyclopropyl-6-{4-[2-(trifluoromethyl)phenoxy]piperidin-1-yl}pyridazine-3-carboxamide The title compound was prepared in the same manner as described for Example 4, Step 3 from 6-{4-[2-(trifluoromethyl)phenoxy]piperidin-1-yl}pyridazine-3-carboxylic acid and cyclopropylamine. $^1$H NMR (400 MHz, acetone-d$_6$): δ 0.71-0.82 (m, 4H), 1.91-1.99 (m, 2H), 2.13-2.19 (m, 2H), 2.96-3.02 (m, 1H), 3.91-4.07 (m, 4H), 5.04 (m, 1H), 7.13 (t, 1H), 7.37 (m, 2H), 7.62-7.68 (m, 2H), 7.91 (d, 1H), 8.09 (s, 1H). MS (+ESI) m/z 407 (MH$^+$).

EXAMPLE 6

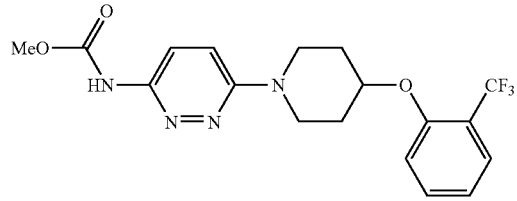

Methyl (6-{4-[2-(trifluoromethyl)phenoxy]piperidin-1-yl}pyridazin-3-yl)carbamate A mixture of 6-{4-[2-(trifluoromethyl)phenoxy]piperidin-1-yl}pyridazine-3-carboxylic acid (150 mg, 0.4 mmol), DPPA (100 µL, 0.46 mmol) and Et$_3$N (65 µL, 0.46 mmol) in DMF (1.5 mL) was stirred at r.t. overnight. MeOH (150 µL, 3.7 mmol) was then added and the mixture was heated at 65-70° C. for 6 h. After cooling, the mixture was diluted with water and extracted with EtOAc. The EtOAc extract was washed twice with water, dried (Na$_2$SO$_4$) and concentrated. CombiFlash chromatography (10 g, 40-80% EtOAc in hexanes in 20 min, 20 mL/min, 15 mL/fraction) gave the title compound as a white solid. $^1$H NMR (500 MHz, acetone-d$_6$): δ 1.89-1.97 (m, 2H), 2.15 (m, 2H), 3.65-3.71 (m, 2H), 3.76 (s, 3H), 3.87-3.93 (m, 2H), 4.94-4.98 (m, 1H), 7.11 (t, 1H), 7.37 (m, 2H), 7.61-7.67 (m, 2H), 8.00 (d, 1H), 9.11 (s, 1H). MS (+ESI) m/z 397 (MH⁺).

EXAMPLE 7

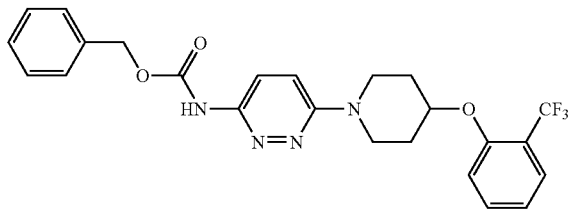

Benzyl (6-{4-[2-(trifluoromethyl)phenoxy]piperidin-1-yl}pyridazin-3-yl)carbamate The title compound was prepared in the same manner as described for Example 6 from 6-{4-[2-(trifluoromethyl)phenoxy]piperidin-1-yl}pyridazine-3-carboxylic acid and benzyl alcohol. ¹H NMR (400 MHz, acetone-d₆): δ 1.88-1.94 (m, 2H), 2.08-2.18 (m, 2H), 3.66-3.72 (m, 2H), 3.88-3.94 (m, 2H), 4.95-4.99 (m, 1H), 5.25 (s, 2H), 7.11 (t, 1H), 7.34-7.50 (m, 6H), 7.61-7.67 (m, 2H), 8.03 (d, 1H), 9.28 (s, 1H). MS (+ESI) m/z 473 (MH+).

EXAMPLE 8

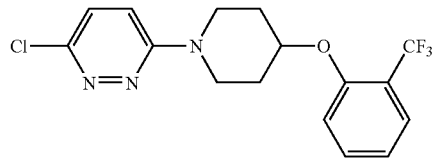

3-Chloro-6-{4-[2-(trifluoromethyl)phenoxy]piperidin-1-yl}pyridazine

The title compound was prepared in the same manner as described for Example 1 Step 3 from 4-[2-(trifluoromethyl)phenoxy]piperidine and 3,6-dichloropyridazine. ¹H NMR (400 MHz, acetone-d₆): δ 1.89-1.99 (m, 2H), 2.11-2.23 (m, 3H), 3.78-3.84 (m, 2H), 3.91-3.97 (m, 2H), 4.98-5.04 (m, 1H), 7.12 (t, 1H), 7.41 (q, 3H), 7.61-7.67 (m, 2H). MS (+ESI) m/z 358 (MH⁺).

EXAMPLE 9

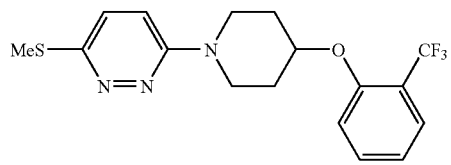

3-(Methylthio)-6-{4-[2-(trifluoromethyl)phenoxy]piperidin-1-yl}pyridazine

A mixture of 3-chloro-6-{4-[2-(trifluoromethyl)phenoxy]piperidin-1-yl}pyridazine (1.9 g, 5.3 mmol) and NaSMe (558 mg, 7.9 mmol) in DMF (27 mL) was heated at 80° C. After 2 h, the mixture was diluted with sat. aq. NaHCO₃ (50 mL), extracted with (3×25 mL) EtOAc and dried over Na₂SO₄. Evaporation of the solvent followed by purification by Combiflash chromatography (SiO₂, gradient elution 20-50% EtOAc/Hexanes) afforded the desired product. ¹H NMR (500 MHz, acetone-d₆): δ 1.87-1.95 (m, 2H), 2.09-2.19 (m, 2H), 2.61 (s, 3H), 3.69-3.75 (m, 2H), 3.88-3.94 (m, 2H), 4.95-4.99 (m, 1H), 7.11 (t, 1H), 7.23 (d, 1H), 7.28 (d, 1H), 7.37 (d, 1H), 7.60-7.66 (m, 2H). MS (+ESI) m/z 370 (MH⁺).

EXAMPLE 10

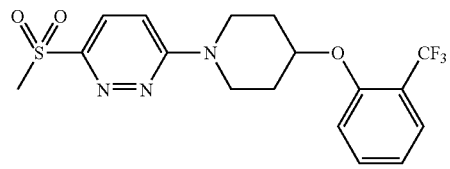

3-(Methylsulfonyl)-6-{4-[2-(trifluoromethyl)phenoxy]piperidin-1-yl}pyridazine

To a mixture of 3-(methylthio)-6-{4-[2-(trifluoromethyl)phenoxy]piperidin-1-yl}pyridazine (2.1 g, 5.7 mmol), Na₂WO₄.2H₂O (19 mg, 56.9 mmol) and Bu₄NHSO₄ (97 mg, 0.28 mmol) in EtOAc (57 mL) was added H₂O₂ (30% in water, 1.4 mL, 14.2 mmol). The mixture was stirred at room temperature. After 2 h, 0.5 mL of H₂O₂ was added and the mixture was further stirred for 4 h, diluted with sodium thiosulfate (10%, 20 mL), extracted with (3×25 mL) of EtOAc and dried over Na₂SO₄. Evaporation of the solvent followed by purification by Combiflash chromatography (SiO₂, gradient elution 30-70% EtOAc/Hexanes) afforded the desired product. ¹H NMR (500 MHz, acetone-d₆): δ 1.94-2.00 (m, 2H), 2.15-2.21 (m, 2H), 3.29 (s, 3H), 4.06 (dd, 4H), 5.05-5.07 (m, 1H), 7.12 (t, 1H), 7.41 (dd, 2H), 7.62-7.68 (m, 2H), 7.84 (d, 1H). MS (+ESI) m/z 402 (MH⁺).

EXAMPLE 11

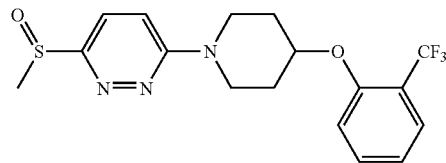

3-(Methylsulfinyl)-6-{4-[2-(trifluoromethyl)phenoxy]piperidin-1-yl}pyridazine

To a solution of 3-(methylthio)-6-{4-[2-(trifluoromethyl)phenoxy]piperidin-1-yl}pyridazine (1.62 g, 4.39 mmol) in CH₂Cl₂/MeOH (2:1, 22 mL) was added magnesium monoperoxyphthalate (1.3 g, 2.2 mmol). The mixture was stirred at room temperature for 18 h. Additional magnesium monoperoxyphthalate (300 mg) was added and after 1 h, the mixture was diluted with saturated aqueous NaHCO₃ (50 mL), extracted with (3×20 mL) of EtOAc and dried over Na₂SO₄.

Evaporation of the solvent followed by purification by Combiflash chromatography (SiO$_2$, eluant 5% MeOH/EtOAc) afforded the desired product. $^1$H NMR (500 MHz, acetone-d$_6$): δ 1.92-1.98 (m, 2H), 2.14-2.18 (m, 2H), 2.84 (s, 3H), 3.90-4.08 (m, 5H), 5.01-5.03 (m, 1H), 7.11 (t, 1H), 7.38 (d, 1H), 7.51 (d, 1H), 7.61-7.67 (m, 2H), 7.82 (d, 1H). MS (+ESI) m/z 386 (MH$^+$).

EXAMPLE 12

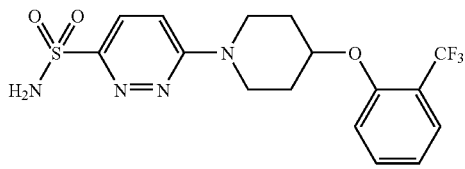

6-{4-[2-(Trifluoromethyl)phenoxy]piperidin-1-yl}pyridazine-3-sulfonamide

A mixture of 3-(methylsulfinyl)-6-{4-[2-(trifluoromethyl)phenoxy]piperidin-1-yl}pyridazine (550 mg, 1.42 mmol) in Ac$_2$O (5 mL) and NaOAc (582 mg, 4.3 mmol) was heated at 140° C. for 2 h. The volatiles were evaporated and the residue was dissolved and re-evaporated with (3×5 mL) of benzene. The product was dried under high vacuum and dissolved in CH$_2$Cl$_2$/MeOH (2:1, 7 mL) followed by addition of magnesium monoperoxyphthalate (1.0 g, 1.72 mmol). The reaction mixture was stirred for 16 h after which it was filtered and the filtrate washed with saturated aqueous NaHCO$_3$ (50 mL), dried over Na$_2$SO$_4$ and evaporated. The residue was dissolved in THF/MeOH (2:1, 7 mL) and treated with aqueous NaOH (1.4 mL, 1.42 mmol, 1N) and stirred for 1 h. The solvent was evaporated and the residue dissolved and re-evaporated with (2×5 mL) of EtOH and then benzene (5 mL). The mixture was dried under high vacuum, triturated with Et$_2$O (2×5 mL). CH$_2$Cl$_2$ (5 mL) was added and the mixture was cooled to 0° C. SO$_2$Cl$_2$ (0.11 mL, 1.42 mmol) was added and the mixture was stirred at room temperature for 1 h. The mixture was then cooled to 0° C., treated with aqueous NH$_3$ (5 mL) and warmed to room temperature. After 1 h, the mixture was diluted with water (5 mL), extracted with (3×20 mL) of EtOAc and dried over Na$_2$SO$_4$. Evaporation of the solvent followed by purification by Combiflash chromatography (SiO$_2$, gradient elution 40-60% EtOAc/hexanes) afforded the desired product. $^1$H NMR (500 MHz, acetone-d$_6$): δ 1.94-1.98 (m, 2H), 2.14-2.20 (m, 2H), 3.95-4.09 (m, 4H), 5.03-5.05 (m, 1H), 6.69 (s, 2H), 7.12 (t, 1H), 7.39 (d, 2H), 7.62-7.68 (m, 2H), 7.79 (d, 1H). MS (+ESI) m/z 403 (MH$^+$).

EXAMPLE 13

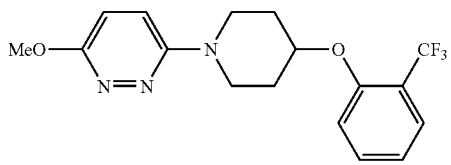

3-Methoxy-6-{4-[2-(trifluoromethyl)phenoxy]piperidin-1-yl}pyridazine

A solution of 3-chloro-6-{4-[2-(trifluoromethyl)phenoxy]piperidin-1-yl}pyridazine (150 mg, 0.42 mmol) in MeOH (1 mL) and NaOMe (2.5 mL, 0.87 mmol, 25-30% in MeOH) was heated at 80° C. After 4 h, solvent was evaporated and the mixture was diluted with water (3 mL), extracted with EtOAc (3×2 mL) and dried over Na$_2$SO$_4$. Evaporation of the solvent followed by purification Combiflash chromatography (SiO$_2$, eluant 30-40% EtOAc/hexanes) afforded the desired product. $^1$H NMR (500 MHz, acetone-d$_6$): δ 1.87-1.95 (m, 2H), 2.07-2.14 (m, 2H), 3.58-3.64 (m, 2H), 3.78-3.86 (m, 2H), 3.97 (s, 3H), 4.90-5.00 (m, 1H), 6.94 (d, 1H), 7.08-7.12 (m, 1H), 7.35 (t, 2H), 7.59-7.65 (m, 2H). MS (+ESI) m/z 354 (MH$^+$).

EXAMPLE 14

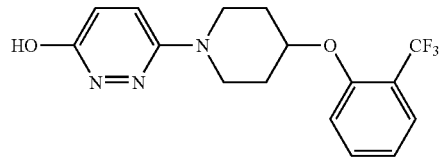

6-{4-[2-(Trifluoromethyl)phenoxy]piperidin-1-yl}pyridazin-3-ol

A solution of 3-chloro-6-{4-[2-(trifluoromethyl)phenoxy]piperidin-1-yl}pyridazine (100 mg, 0.28 mmol) and KOAc (55 mg, 0.56 mmol) in AcOH/H$_2$O (1:1, 2 mL) was heated at 150° C. After 3 h, the solvent was evaporated and the mixture diluted with water (2 mL), extracted with (3×2 mL) EtOAc and dried over Na$_2$SO$_4$. Evaporation of the solvent followed by purification Combiflash chromatography (SiO$_2$, eluant 5% MeOH/EtOAc) afforded the desired product. $^1$H NMR (500 MHz, acetone-d$_6$): δ 1.86-1.93 (m, 2H), 2.10-2.14 (m, 2H), 3.33-3.39 (m, 2H), 3.54-3.60 (m, 2H), 4.88-4.90 (m, 1H), 6.77 (d, 1H), 7.10 (t, 1H), 7.34 (d, 1H), 7.49 (d, 1H), 7.59-7.65 (m, 2H). MS (+ESI) m/z 340 (MH$^+$).

EXAMPLE 15

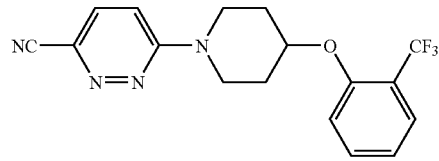

6-{4-[2-(Trifluoromethyl)phenoxy]piperidin-1-yl}pyridazine-3-carbonitrile

To a solution of 6-{4-[2-(trifluoromethyl)phenoxy]piperidin-1-yl}pyridazine-3-carboxamide (1.35 g, 3.69 mmol) and pyridine (1.49 mL, 18.43 mmol) in 1,4-dioxane (30 mL) at 0° C. was added trifluoroacetic anhydride (1.04 mL, 7.37 mmol). The mixture was warmed to room temperature and stirred for 2 days. Aqueous saturated NaHCO$_3$ and ethyl acetate were added. The layers were separated and the aqueous phase was extracted four times with ethyl acetate. The combined organic extracts were washed with brine, dried (NaSO$_4$) and concentrated. Purification by silica gel chromatography (gradient 60% ethyl acetate:hexanes to 100% ethyl acetate) provided the title compound. $^1$H NMR (acetone-d$_6$) δ 7.75 (1H, d, J=9.6 Hz), 7.68-7.62 (2H, m), 7.37 (2H, dd, J=8.4, 13.9 Hz), 7.13 (1H, t, J=7.6 Hz), 5.08-5.04 (1H, m), 4.06-4.02 (4H, m), 2.20-2.14 (2H, m), 2.00-1.94 (2H, m).

EXAMPLE 16

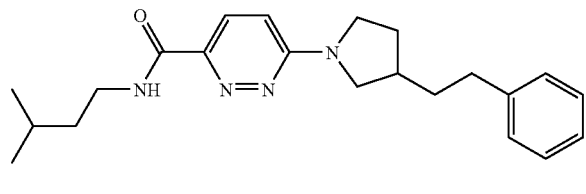

N-(3-Methylbutyl)-6-[3-(2-phenylethyl)pyrrolidin-1-yl]pyridazine-3-carboxamide

To a solution of 6-chloro-N-(3-methylbutyl)pyridazine-3-carboxamide (20 mg, 0.088 mmol) and 3-(2-phenylethyl)pyrrolidine (23 mg, 0.13 mmol) in 1-methyl-2-pyrrolidinone (1 mL) was added Et$_3$N (25 μL, 0.18 mmol) at room temperature. The mixture was stirred at 120° C. overnight. The reaction was then concentrated and the residue purified using a semi-prep HPLC/MS to give the title compound. MS (+ESI) m/z 367 (MH$^+$).

EXAMPLE 17

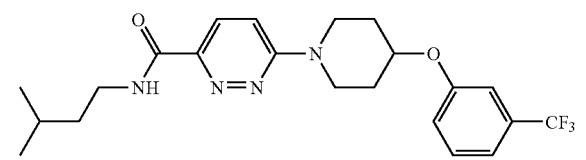

N-(3-Methylbutyl)-6-{4-[3-(trifluoromethyl)phenoxy]piperidin-1-yl}pyridazine-3-carboxamide The title compound was prepared in the same manner as described for Example 16 from 6-chloro-N-(3-methylbutyl)pyridazine-3-carboxamide and 4-[3-(trifluoromethyl)phenoxy]piperidine. MS (+ESI) m/z 437 (MH$^+$).

EXAMPLE 18

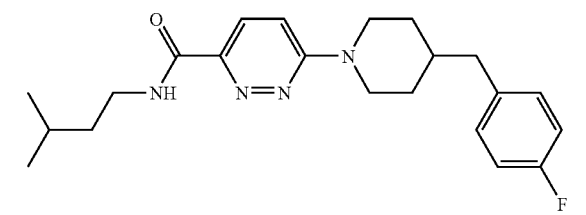

6-[4-(4-Fluorobenzyl)piperidin-1-yl]-N-(3-methylbutyl)pyridazine-3-carboxamide

The title compound was prepared in the same manner as described for Example 16 from 6-chloro-N-(3-methylbutyl)pyridazine-3-carboxamide and 4-(4-fluorobenzyl)piperidine. MS (+ESI) m/z 385 (MH$^+$).

EXAMPLE 19

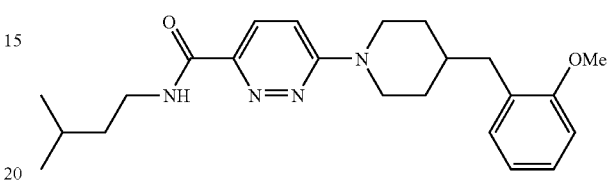

6-[4-(2-Methoxybenzyl)piperidin-1-yl]-N-(3-methylbutyl)pyridazine-3-carboxamide

The title compound was prepared in the same manner as described for Example 16 from 6-chloro-N-(3-methylbutyl)pyridazine-3-carboxamide and 4-(2-methoxybenzyl)piperidine. MS (+ESI) m/z 397 (MH$^+$).

EXAMPLE 20

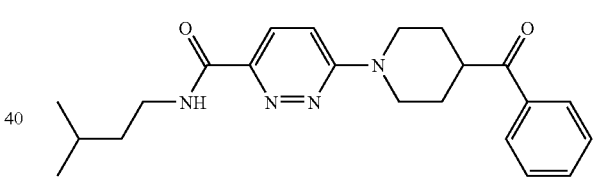

6-(4-Benzoylpiperidin-1-yl)-N-(3-methylbutyl)pyridazine-3-carboxamide

The title compound was prepared in the same manner as described for Example 16 from 6-chloro-N-(3-methylbutyl)pyridazine-3-carboxamide and phenyl(piperidin-4-yl)methanone. MS (+ESI) m/z 381 (MH$^+$).

EXAMPLE 21

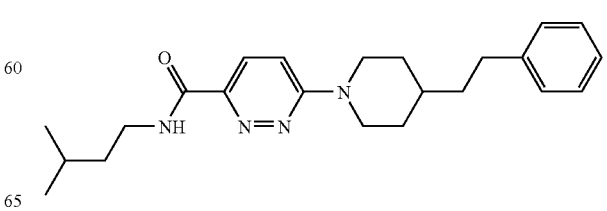

N-(3-Methylbutyl)-6-[4-(2-phenylethyl)piperidin-1-yl]pyridazine-3-carboxamide The title compound was prepared in the same manner as described for Example 16 from 6-chloro-N-(3-methylbutyl)pyridazine-3-carboxamide and 4-(2-phenylethyl)piperidine. MS (+ESI) m/z 381 (MH+).

EXAMPLE 22

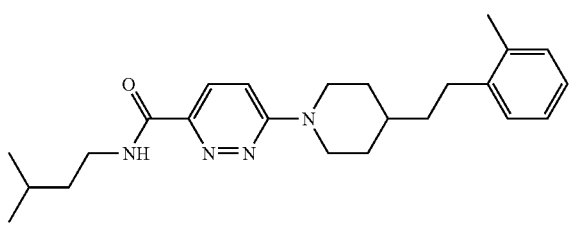

N-(3-Methylbutyl)-6-{4-[2-(2-methylphenyl)ethyl]piperidin-1-yl}pyridazine-3-carboxamide The title compound was prepared in the same manner as described for Example 16 from 6-chloro-N-(3-methylbutyl)pyridazine-3-carboxamide and 4-[2-(2-methylphenyl)ethyl]piperidine. MS (+ESI) m/z 395 (MH+).

EXAMPLE 23

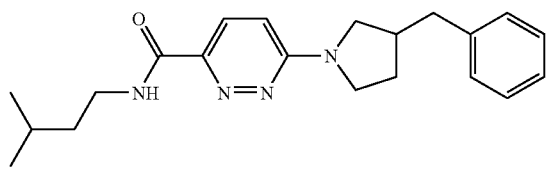

6-(3-Benzylpyrrolidin-1-yl)-N-(3-methylbutyl)pyridazine-3-carboxamide

The title compound was prepared in the same manner as described for Example 16 from 6-chloro-N-(3-methylbutyl)pyridazine-3-carboxamide and 3-benzylpyrrolidine. MS (+ESI) m/z 353 (MH+).

EXAMPLE 24

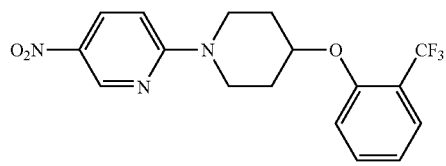

5-Nitro-2-{4-[2-(trifluoromethyl)phenoxy]piperidin-1-yl}pyridine

A mixture of 2-chloro-5-nitropyridine (1.6 g, 6.5 mmol), 4-[2-(trifluoromethyl)phenoxy]piperidine (1.2 g, 7.6 mmol), and DBU (2 mL, 13 mmol) in DMF (25 mL) was heated at 80-85° C. for 2 h. The EtOAc extract was washed three times with water, dried (MgSO$_4$) and concentrated. CombiFlash chromatography (120 g, 20-40% EtOAc in hexanes in 20 min, 70 mL/min, 18 mL/fraction) gave the desired product as a yellow powder.

$^1$H NMR (400 MHz, acetone-d$_6$): δ 9.00 (d, 1H), 8.26 (dd, 1H), 7.68-7.62 (m, 2H), 7.39 (d, 1H), 7.13 (t, 1H), 7.00 (d, 1H), 5.08-5.04 (m, 1H), 4.03 (t, 4H), 2.19-2.13 (m, 2H), 1.99-1.93 (m, 2H); MS (+ESI) m/z 368 (MH+).

EXAMPLE 25

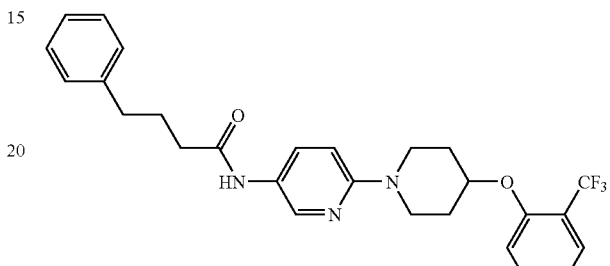

4-Phenyl-N-(6-{4-[2-(trifluoromethyl)phenoxy]piperidin-1-yl}pyridin-3-yl)butanamide Step 1: 6-{4-[2-(trifluoromethyl)phenoxy]piperidin-1-yl}pyridin-3-amine A mixture of 5-nitro-2-{4-[2-(trifluoromethyl)phenoxy]piperidin-1-yl}pyridine (1.6 g, 4.4 mmol) and 10% Pd/C (300 mg) in EtOAc (100 mL) was hydrogenated at 50 psi overnight. The catalyst was filtered off through celite. The filtrate was removed in vacuo to give the title compound as a light brown gum.

$^1$H NMR (400 MHz, acetone-d$_6$): δ 7.76 (d, 1H), 7.65-7.59 (m, 2H), 7.35 (d, 1H), 7.12-7.02 (m, 2H), 6.71 (d, 1H), 4.88-4.82 (m, 1H), 4.18 (s, 2H), 3.76-3.70 (m, 2H), 3.40-3.34 (m, 2H), 2.11-2.00 (m, 2H), 1.89-1.81 (m, 2H).

Step 2: 4-Phenyl-N-(6-{4-[2-(trifluoromethyl)phenoxy]piperidin-1-yl}pyridin-3-yl)butanamide A mixture of 6-{4-[2-(trifluoromethyl)phenoxy]piperidin-1-yl}pyridin-3-amine (225 mg, 0.7 mmol), 4-phenylbutyric acid (131 mg, 0.8 mmol), HATU (380 mg, 1.5 mmol) and DIPEA (465 μL, 2.7 mmol) in DMF (10 mL) was stirred at room temperature for 4 h. After dilution with water, the mixture was extracted with EtOAc. The EtOAc extract was washed with diluted brine, dried (Na$_2$SO$_4$) and concentrated. CombiFlash chromatography (10 g, 40-70% EtOAc in hexanes in 20 min, 20 mL/min, 15 mL/fraction) gave a light brown gum which solidified on standing. Swishing with hexanes-Et$_2$O (1:1) gave the title compound as a white powder.

$^1$H NMR (400 MHz, acetone-d$_6$): δ 8.96 (s, 1H), 8.35 (d, 1H), 7.95-7.91 (m, 1H), 7.63 (m, 2H), 7.37-7.19 (m, 6H), 7.10 (t, 1H), 6.85 (d, 1H), 4.95-4.89 (m, 1H), 3.89-3.83 (m, 2H), 3.60-3.54 (m, 2H), 2.70 (t, 2H), 2.39 (t, 2H), 2.11-1.99 (m, 4H), 1.92-1.82 (m, 2H); MS (+ESI) m/z 484 (MH+).

EXAMPLE 26

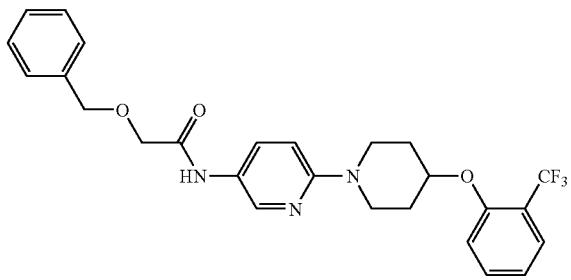

2-(Benzyloxy)-N-(6-{4-[2-(trifluoromethyl)phenoxy]piperidin-1-yl}pyridin-3-yl)acetamide The title compound was prepared in the same manner as described for Example 25, step 2 from 6-{4-[2-(trifluoromethyl)phenoxy]piperidin-1-yl}pyridin-3-amine and benzyloxyacetic acid.

$^1$H NMR (400 MHz, acetone-$d_6$): δ 8.98 (s, 1H), 8.44 (d, 1H), 7.93 (dd, 1H), 7.66-7.60 (m, 2H), 7.48-7.34 (m, 6H), 7.11 (t, 1H), 6.87 (d, 1H), 4.92 (m, 1H), 4.71 (s, 2H), 4.11 (s, 2H), 3.90-3.84 (m, 2H), 3.63-3.57 (m, 2H), 2.20-2.10 (m, 2H), 1.89-1.83 (m, 2H). MS (+ESI) m/z 486 (MH$^+$).

EXAMPLES 27-41 were prepared following the general procedure described below:

A stock solution was prepared from 6-{4-[2-(trifluoromethyl)benzoyl]piperazin-1-yl}pyridazine-3-carboxylic acid (1.85 g), 4-methylmorpholine (4.5 mL) and 1-propylphosphonic acid cyclic anhydride (3.6 mL) in 45 mL of DMF. The total volume was 53 mL, which corresponded to 35 mg/mL of 6-{4-[2-(trifluoromethyl)benzoyl]piperazin-1-yl}pyridazine-3-carboxylic acid.

Each reaction was carried out with 600 μL of the stock solution (20 mg of 6-{4-[2-(trifluoromethyl)benzoyl]piperazin-1-yl}pyridazine-3-carboxylic acid) with 4.0 equivalents of the corresponding amine and stirred over night at room temperature. After quenching with 150 μL of acetic acid, the mixture was evaporated. The residue was diluted with DMSO and purified by LC-MS to give the final product. Compounds with a BOC protecting group were taken in CH$_2$Cl$_2$ and treated with trifluoroacetic acid prior to evaporation and purification on LC-MS.

EXAMPLE 27

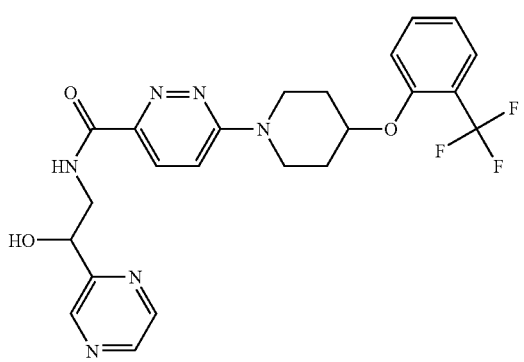

N-(2-Hydroxy-2-pyrazin-2-ylethyl)-6-{4-[2-(trifluoromethyl)phenoxy]piperidin-1-yl}pyridazine-3-carboxamide MS (+ESI) m/z 489 (MH+).

EXAMPLE 28

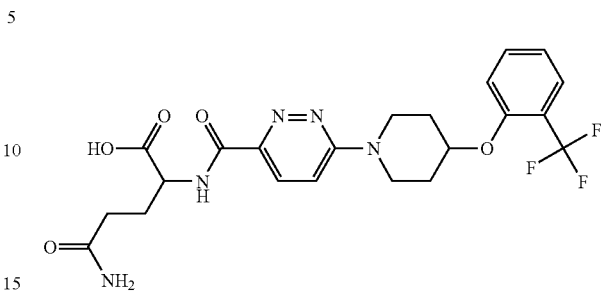

N$^2$-[(6-{4-[2-(Trifluoromethyl)phenoxy]piperidin-1-yl}pyridazin-3-yl)carbonyl]glutamine MS (+ESI) m/z 496 (MH+).

EXAMPLE 29

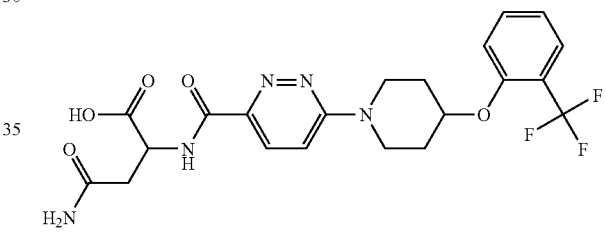

N$^2$-[(6-{4-[2-(Trifluoromethyl)phenoxy]piperidin-1-yl}pyridazin-3-yl)carbonyl]asparagine MS (+ESI) m/z 482 (MH+).

EXAMPLE 30

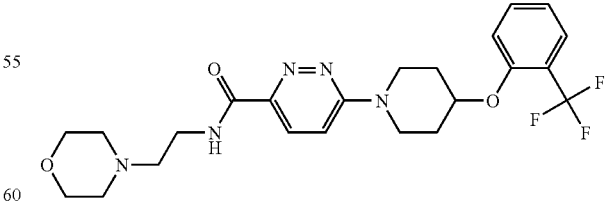

N-(2-Morpholin-4-ylethyl)-6-{4-[2-(trifluoromethyl)phenoxy]piperidin-1-yl}pyridazine-3-carboxamide MS (+ESI) m/z 480 (MH+).

EXAMPLE 31

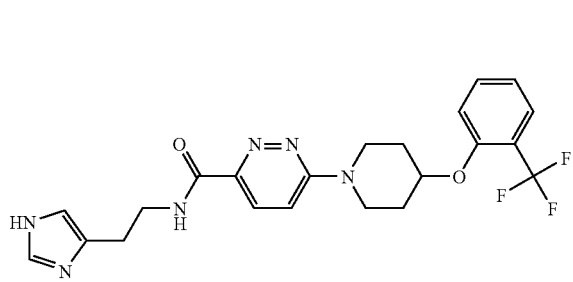

N-[2-(1H-Imidazol-4-yl)ethyl]-6-{4-[2-(trifluoromethyl)phenoxy]piperidin-1-yl}pyridazine-3-carboxamide MS (+ESI) m/z 461 (MH+).

EXAMPLE 32

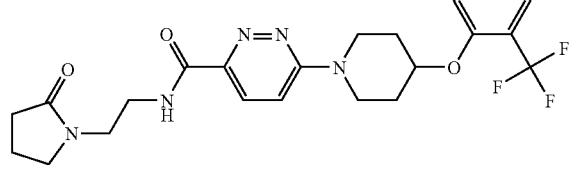

N-[2-(2-Oxopyrrolidin-1-yl)ethyl]-6-{4-[2-(trifluoromethyl)phenoxy]piperidin-1-yl}pyridazine-3-carboxamide MS (+ESI) m/z 478 (MH+).

EXAMPLE 33

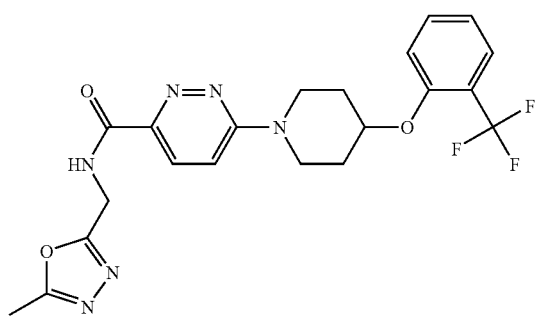

N-[(5-Methyl-1,3,4-oxadiazol-2-yl)methyl]-6-{4-[2-(trifluoromethyl)phenoxy]piperidin-1-yl}pyridazine-3-carboxamide MS (+ESI) m/z 463 (MH+).

EXAMPLE 34

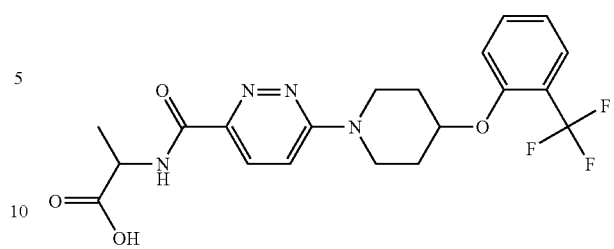

N-[(6-{4-[2-(Trifluoromethyl)phenoxy]piperidin-1-yl}pyridazin-3-yl)carbonyl]alanine MS (+ESI) m/z 439 (MH+).

EXAMPLE 35

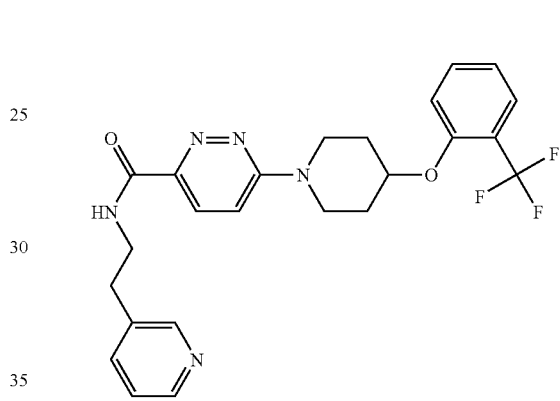

N-(2-Pyridin-3-ylethyl)-6-{4-[2-(trifluoromethyl)phenoxy]piperidin-1-yl}pyridazine-3-carboxamide MS (+ESI) m/z 472 (MH+).

EXAMPLE 36

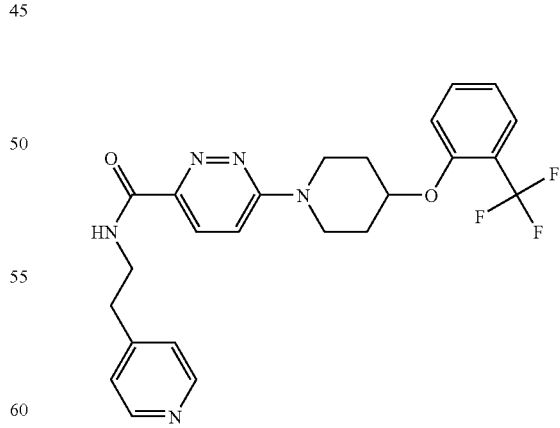

N-(2-Pyridin-4-ylethyl)-6-{4-[2-(trifluoromethyl)phenoxy]piperidin-1-yl}pyridazine-3-carboxamide MS (+ESI) m/z 472 (MH+).

EXAMPLE 37

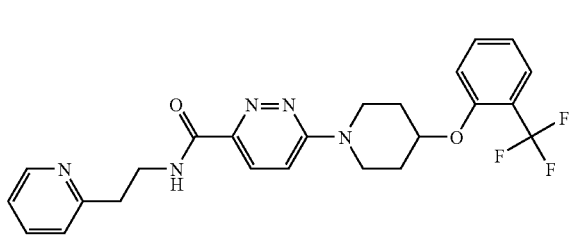

N-(2-Pyridin-2-ylethyl)-6-{4-[2-(trifluoromethyl)phenoxy]piperidin-1-yl}pyridazine-3-carboxamide MS (+ESI) m/z 472 (MH+).

EXAMPLE 38

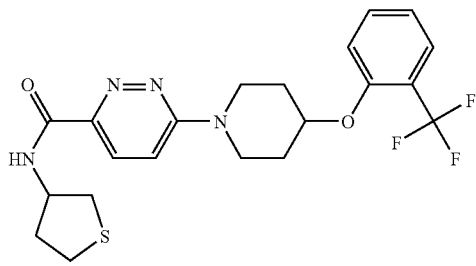

N-(Tetrahydro-3-thienyl)-6-{4-[2-(trifluoromethyl)phenoxy]piperidin-1-yl}pyridazine-3-carboxamide MS (+ESI) m/z 453 (MH+).

EXAMPLE 39

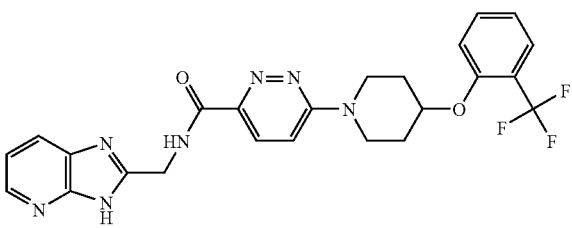

N-(3H-Imidazo[4,5-b]pyridin-2-ylmethyl)-6-{4-[2-(trifluoromethyl)phenoxy]piperidin-1-yl}pyridazine-3-carboxamide MS (+ESI) m/z 498 (MH+).

Example 40

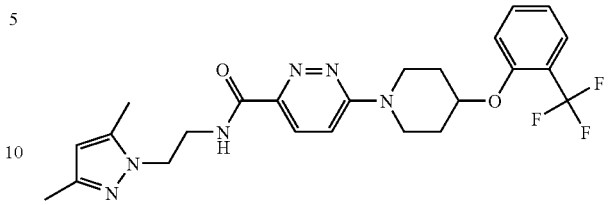

N-[2-(3,5-Dimethyl-1H-pyrazol-1-yl)ethyl]-6-{4-[2-(trifluoromethyl)phenoxy]piperidin-1-yl}pyridazine-3-carboxamide MS (+ESI) m/z 489 (MH+).

EXAMPLE 41

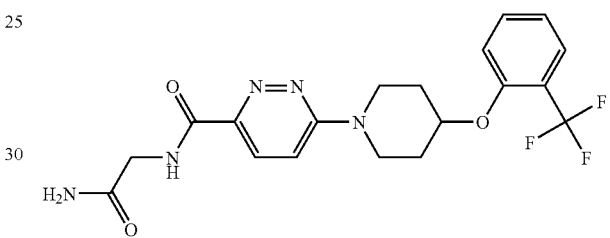

N-(2-Amino-2-oxoethyl)-6-{4-[2-(trifluoromethyl)phenoxy]piperidin-1-yl}pyridazine-3-carboxamide MS (+ESI) m/z 424 (MH+).

EXAMPLE OF A PHARMACEUTICAL FORMULATION

As a specific embodiment of an oral composition of a compound of the present invention, 50 mg of the compound of any of the Examples is formulated with sufficient finely divided lactose to provide a total amount of 580 to 590 mg to fill a size O hard gelatin capsule.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for a particular condition. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:

1. A compound of structural formula I:

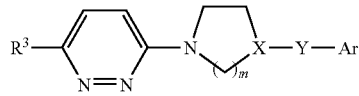

or a pharmaceutically acceptable salt thereof; wherein
each n is independently 0, 1, 2, or 3;
each p is independently 0, 1, or 2;
m is 2;
q is 1 or 2;
X—Y is CH—O, CH—S(O)$_p$, CH—NR$^6$, CH—C(R$^1$R$^2$)$_q$, or CH—C(O);
Ar is phenyl, naphthyl, or heteroaryl unsubstituted or substituted with one to five R$^8$ substituents;
R$^1$ and R$^2$ are each independently hydrogen or C$_{1-3}$ alkyl, wherein alkyl is unsubstituted or substituted with one to three substituents independently selected from fluorine and hydroxy;
R$^3$ is independently selected from the group consisting of
C(O)NR$^4$R$^5$,
OC(O)NR$^4$R$^5$,
SO$_2$NR$^4$R$^5$,
NR$^7$SO$_2$R$^6$,
NR$^7$C(O)NR$^4$R$^5$,
NR$^7$C(O)R$^6$, and
NR$^7$CO$_2$R$^6$;
in which cycloalkyl is unsubstituted or substituted with one to three substituents independently selected from halogen, hydroxy, C$_{1-4}$ alkyl, trifluoromethyl, and C$_{1-4}$ alkoxy;
R$^4$ and R$^5$ are each independently selected from the group consisting of
hydrogen,
C$_{1-8}$ alkyl,
(CH$_2$)$_n$-phenyl,
(CH$_2$)$_n$-heteroaryl,
(CH$_2$)$_n$-naphthyl, and
(CH$_2$)$_n$C$_{3-7}$ cycloalkyl;
wherein alkyl, phenyl, heteroaryl, and cycloalkyl are unsubstituted or substituted with one to three groups independently selected from halogen, hydroxy, C$_{1-4}$ alkyl, and C$_{1-4}$ alkoxy; or R$^4$ and R$^5$ together with the nitrogen atom to which they are attached form a 4- to 8-membered mono- or bicyclic ring system optionally containing an additional heteroatom selected from O, S, NH, and NC$_{1-4}$ alkyl;
each R$^6$ is independently C$_{1-6}$ alkyl, wherein alkyl is unsubstituted or substituted with one to five substituents independently selected from halogen and hydroxyl;
R$^7$ is hydrogen or R$^6$; and
each R$^8$ is independently selected from the group consisting of
C$_{1-6}$ alkyl,
(CH$_2$)$_n$-phenyl,
(CH$_2$)$_n$-naphthyl,
(CH$_2$)$_n$-heteroaryl,
(CH$_2$)$_n$-heterocyclyl,
(CH$_2$)$_n$C$_{3-7}$ cycloalkyl,
halogen,
OR$^4$,
(CH$_2$)$_n$NR$^4$R$^5$,
(CH$_2$)$_n$C≡N,
(CH$_2$)$_n$CO$_2$R$^4$,
NO$_2$,
(CH$_2$)$_n$NR$^7$SO$_2$R$^6$,
(CH$_2$)$_n$SO$_2$NR$^4$R$^5$,
(CH$_2$)$_n$S(O)$_p$R$^6$,
(CH$_2$)$_n$NR$^7$C(O)NR$^4$R$^5$,
(CH$_2$)$_n$C(O)NR$^4$R$^5$,
(CH$_2$)$_n$NR$^7$C(O)R$^6$,
(CH$_2$)$_n$NR$^7$CO$_2$R$^6$,
O(CH$_2$)$_n$C(O)NR$^4$R$^5$,
CF$_3$,
CH$_2$CF$_3$,
OCF$_3$, and
OCH$_2$CF$_3$;
in which phenyl, naphthyl, heteroaryl, cycloalkyl, and heterocyclyl are unsubstituted or substituted with one to three substituents independently selected from halogen, hydroxy, C$_{1-4}$ alkyl, trifluoromethyl, and C$_{1-4}$ alkoxy; and wherein any methylene (CH$_2$) carbon atom in R$^8$ is unsubstituted or substituted with one to two groups independently selected from halogen, hydroxy, and C$_{1-4}$ alkyl; or two substituents when on the same methylene (CH$_2$) group are taken together with the carbon atom to which they are attached to form a cyclopropyl group.

2. The compound of claim 1 wherein X—Y is CH—O and Ar is phenyl unsubstituted or substituted with one to three R$^8$ substituents.

3. The compound of claim 1 wherein X—Y is CH—CR$^1$R$^2$ and Ar is phenyl unsubstituted or substituted with one to three R$^8$ substituents.

4. The compound of claim 1 wherein X—Y is CH—(CR$^1$R$^2$)$_2$ and Ar is phenyl unsubstituted or substituted with one to three R$^8$ substituents.

5. A compound selected from the group consisting of:

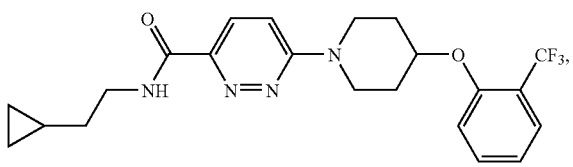

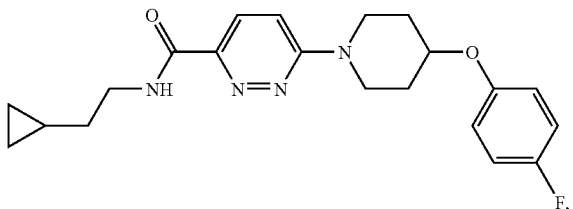

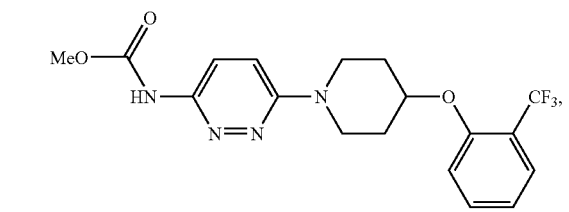

-continued
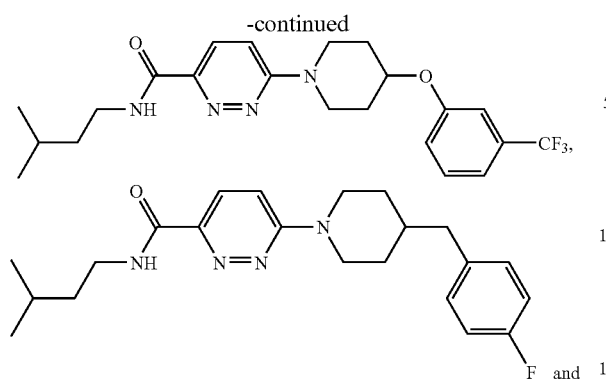
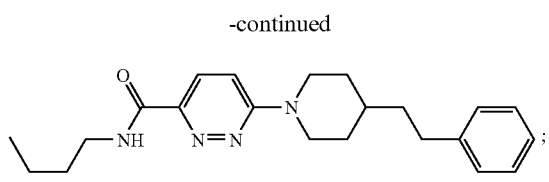
or a pharmaceutically acceptable salt thereof.
6. A pharmaceutical composition comprising a compound in accordance with claim 1 in combination with a pharmaceutically acceptable carrier.
* * * * *